(12) United States Patent
Yoshiki et al.

(10) Patent No.: US 8,114,588 B2
(45) Date of Patent: Feb. 14, 2012

(54) METHOD FOR DETECTING VESICOURETERAL REFLUX OR INTERSTITIAL CYSTITIS

(75) Inventors: Tatsuhiro Yoshiki, Shiga (JP); Susumu Kageyama, Kyoto (JP); Hideaki Iwaki, Shiga (JP)

(73) Assignee: TSS Biotech Inc., Tokyo (JP)

( * ) Notice: Subject to any disclaimer, the term of this patent is extended or adjusted under 35 U.S.C. 154(b) by 182 days.

(21) Appl. No.: 11/181,830

(22) Filed: Jul. 15, 2005

(65) Prior Publication Data

US 2007/0015167 A1    Jan. 18, 2007

(51) Int. Cl.
 *C12Q 1/68* (2006.01)
 *C12P 19/34* (2006.01)
 *C12M 1/36* (2006.01)
(52) U.S. Cl. ............... 435/6; 435/91.2; 435/287.1
(58) Field of Classification Search .................. None
See application file for complete search history.

(56) References Cited

U.S. PATENT DOCUMENTS 6,277,968 B1    8/2001  Sun et al.
2001/0051344 A1 * 12/2001 Shalon et al. .............. 435/6

OTHER PUBLICATIONS

Olsburgh et al. 2003 Jornal of Pathology vol. 199 p. 41.*
Hu et al. 2000 The Journal of Cell biology vol. 151 p. 961.*
Jiang et al. 2004 Kidney International vol. 66 p. 10.*
Gathwaite 2006 European Urology vol. 49 p. 154.*
Gazzaniga et al. Clinical Cancer Research 2001 vol. 7 p. 577.*
Lucenntini et al. 2004 The Scientist vol. 20 p. 20.*
Kroese et al. Genetics in Medicine 2004 vol. 6 p. 475.*
Kageyama et al. Clinical Chemistry 2004 vol. 50 p. 857.*
Takeshi Yuasa, et al., "Expression of Uroplakin Ib and Uroplakin III Genes in Tissues and Peripheral Blood of Patients with Transistional Cell Carcinoma", Rapid Communication, Jpn. J. Cancer Res. 89, pp. 879-882, Sep. 1998.
Susumu Kageyama, et al., "High Expression of Human Uroplakin Ia in Urinary Bladder Transistional Cell Carcinoma", Jpn. J. Cancer Res. 93, pp. 523-531, May 2002.
Jacques C. Giltay, et al., "No Pathogenic Mutations in the Uroplakin III Gene of 25 Patients with Primary Vesicoureteral Reflux", The Journal of Urology, vol. 171, pp. 931-932, Feb. 2004.
Ping Hu et al., *The Journal of Cell Biology*, vol. 151, No. 5, (Nov. 27, 2000), pp. 961-971.
Zeng, Y. et al., The Journal of Urology, vol. 178, pp. 1322-1327 (2007).
Japanese Office Action issued in Japanese patent application No. 2004-191577 on Mar. 9, 2010.
Liang et al., "Organization of uroplakin subunits: transmembrane topology, pair formation and plaque composition," Biochem. J., vol. 355 (2001) pp. 13-18.
Slobodov et al., "Abnormal expression of molecular markes for bladder impermeability and differentiation in the urothelium of patients with interstitial cystitis," The Journal of Urology, vol. 171, Apr. 2004, pp. 1554-1558.
Strausberg et al., "Accession: BC069544 [GI: 47479545], Definition: *Homosapiens uroplakin* 3A, mRNA (cDNA clone MGC: 97009 IMAGE: 7262218), complete cds." NCBI Sequence Revision History [online]; Jun. 25, 2004, NCBI, URL http://www.ncbi.nlm.nih.gov/viewer/viewer.fcgl?47479545:OLD03:6550485, retreived on Feb. 18, 2010.

* cited by examiner

*Primary Examiner* — Katherine Salmon
(74) *Attorney, Agent, or Firm* — Birch, Stewart, Kolasch & Birch, LLP

(57) ABSTRACT

This invention provides a novel marker of vesicoureteral reflux or interstitial cystitis and a simple and non-invasive method for detecting vesicoureteral reflux or interstitial cystitis. This method comprises detection of uroplakin expression in a sample obtained from a subject.

5 Claims, 6 Drawing Sheets

SEQUENCE LISTING

<160> NUMBER OF SEQ ID NOS: 26

<210> SEQ ID NO 1
<211> LENGTH: 1223
<212> TYPE: DNA
<213> ORGANISM: Homo sapiens

<400> SEQUENCE: 1

```
atggcgtctg cggcagcagc ggaggccgag aagggatctc cagttgtggt gggcctgcta      60
gttgtgggca atatcattat tctgctgtca ggcctgtccc tgtttgctga gaccatatgg     120
gtgacagccg accagtaccg tgtatacccca ctgatgggag tctcaggcaa ggatgacgtc     180
ttcgctggtg cctggattgc catcttctgc ggcttctcct tcttcatggt agccagtttt     240
```

-continued

```
ggtgtgggtg ccgcactctg ccgccgccgg tccatggtcc tcacgtacct ggtgctcatg    300
ctcatcgtct acatcttcga gtgcgcctcc tgcatcacgt cctacaccca ccgtgactac    360
atggtgtcca acccatccct gatcaccaag cagatgctga ccttctacag cgcggacacc    420
gaccagggcc aggagctgac ccgcctctgg gaccgcgtca tgattgagca agaatgctgt    480
ggcacatctg gtcccatgga ctgggtgaac ttcacgtcag ccttccgggc ggccactccg    540
gaggtggtgt tccctggcc cccactgtgc tgtcgccgga cgggaaactt catcccctc     600 aacgaggagg gctgccgcct ggggcacatg gactacctgt caccaaggg ctgcttcgaa     660 cacatcggcc acgccatcga cagctacacg tggggtatct cgtggtttgg gtttgccatc    720
ctgatgtgga cgctcccggt catgctgata gccatgtatt tctacaccat gctctgaggg    780
acaggagggg aaggcaacat acacaccccg gactcctccg catcctcctc ctgcttcctc    840
cgctgggcct ggatggctgc ctcacctctc acctcccaac gtccctagcc cttacgtcct    900
tccacttcca agatcttttt ccaggttcct gagccctact gtgtctcagg tgtgccctga    960
aaccccaggg cttgtgtgca catatcctta gccatctttt caagggacct ctccatgatc   1020
ccacctccca ttcacagata cctctcttgt agctctctga cctcctcctt catggcaggc   1080
atcgccattc ttgctgaacc gtttgtgatt gccatttgag ctctggaagc ctctattgcc   1140
atgagagttc tgtcacggtc actttactgt ccccatcatc acccagcacg gggctaagca   1200
tatactagat agtcaataaa taa                                          1223
```

<210> SEQ ID NO 2
<211> LENGTH: 258
<212> TYPE: PRT
<213> ORGANISM: Homo sapiens

<400> SEQUENCE: 2

```
Met Ala Ser Ala Ala Ala Glu Ala Glu Lys Gly Ser Pro Val Val
  1               5                  10                  15

Val Gly Leu Leu Val Val Gly Asn Ile Ile Leu Leu Ser Gly Leu
                 20                  25                  30

Ser Leu Phe Ala Glu Thr Ile Trp Val Thr Ala Asp Gln Tyr Arg Val
         35                  40                  45

Tyr Pro Leu Met Gly Val Ser Gly Lys Asp Asp Val Phe Ala Gly Ala
     50                  55                  60

Trp Ile Ala Ile Phe Cys Gly Phe Ser Phe Met Val Ala Ser Phe
 65                  70                  75                  80

Gly Val Gly Ala Ala Leu Cys Arg Arg Arg Ser Met Val Leu Thr Tyr
                 85                  90                  95

Leu Val Leu Met Leu Ile Val Tyr Ile Phe Glu Cys Ala Ser Cys Ile
                100                 105                 110

Thr Ser Tyr Thr His Arg Asp Tyr Met Val Ser Asn Pro Ser Leu Ile
            115                 120                 125

Thr Lys Gln Met Leu Thr Phe Tyr Ser Ala Asp Thr Asp Gln Gly Gln
        130                 135                 140

Glu Leu Thr Arg Leu Trp Asp Arg Val Met Ile Glu Gln Glu Cys Cys
145                 150                 155                 160

Gly Thr Ser Gly Pro Met Asp Trp Val Asn Phe Thr Ser Ala Phe Arg
                165                 170                 175

Ala Ala Thr Pro Glu Val Val Phe Pro Trp Pro Leu Cys Cys Arg
            180                 185                 190

Arg Thr Gly Asn Phe Ile Pro Leu Asn Glu Glu Gly Cys Arg Leu Gly
        195                 200                 205
```

His Met Asp Tyr Leu Phe Thr Lys Gly Cys Phe Glu His Ile Gly His
    210                 215                 220

Ala Ile Asp Ser Tyr Thr Trp Gly Ile Ser Trp Phe Gly Phe Ala Ile
225                 230                 235                 240

Leu Met Trp Thr Leu Pro Val Met Leu Ile Ala Met Tyr Phe Tyr Thr
                245                 250                 255

Met Leu

<210> SEQ ID NO 3
<211> LENGTH: 2018
<212> TYPE: DNA
<213> ORGANISM: Homo sapiens

<400> SEQUENCE: 3

```
cgcagaaaga ggaggcgctt gccttcagct tgtgggaaat cccgaagatg ccaaagaca        60
actcaactgt tcgttgcttc cagggcctgc tgattttgg aaatgtgatt attggttgtt       120
gcggcattgc cctgactgcg gagtgcatct tctttgtatc tgaccaacac agcctctacc      180
cactgcttga agccaccgac aacgatgaca tctatgggc tgcctggatc ggcatatttg       240
tgggcatctg cctcttctgc ctgtctgttc taggcattgt aggcatcatg aagtccagca      300
ggaaaattct tctggcgtat tcattctga tgtttatagt atatgccttt gaagtggcat       360
cttgtatcac agcagcaaca caacaagact ttttcacacc caacctcttc ctgaagcaga      420
tgctagagag gtaccaaaac aacagccctc aaacaatga tgaccagtgg aaaaacaatg       480
gagtcaccaa aacctgggac aggctcatgc tccaggacaa ttgctgtggc gtaaatggtc      540
catcagactg gcaaaaatac acatctgcct tccggactga gaataatgat gctgactatc      600
cctggcctcg tcaatgctgt gttatgaaca atcttaaaga acctctcaac ctggaggctt      660
gtaaactagg cgtgcctggt ttttatcaca atcagggctg ctatgaactg atctctggtc      720
caatgaaccg acacgcctgg ggggttgcct ggtttggatt tgccattctc tgctggactt      780
tttgggttct cctgggtacc atgttctact ggagcagaat tgaatattaa gcataaagtg      840
ttgccaccat acctccttcc ccgagtgact ctggatttgg tgctggaacc agctctctcc      900
taatattcca cgtttgtgcc ccacactaac gtgtgtgtct acattgcca agtcagatgg       960
tacgacttc ctttaggatc tcaggcttct gcagttctca tgactcctac ttttcatcct      1020
agtctagcat tctgcaacat ttatatagac tgttgaaagg agaatttgaa aaatgcataa     1080
taactacttc catccctgct tattttaat ttgggaaaat aaatacattc gaaggaacct     1140
gtgttatcac agtaacccag agctgtattt ggctagcaat ctgcctgtat ctctcactat    1200
tatctaaaag aaaccttcca atgcttctgt tgatctcagt attgtcaggg gaacagagaa    1260
gttgggaaaa gattactgaa atataccttt tgcatttctt tctagagtag ctcccatata    1320
tggagatggg tgattctctt gatgccacct tcagatcctt ttattctcca gaataattct    1380
taacagtggt tcaaatttcc tttcatacct gaagtatgt gtttagtagc ctcaattctc     1440
cattaattaa aagtgtgggc tgggcgtggg ggctcatgcc tgtaatccca gcactttggg    1500
aggccgaggt gggcagatca cctgaggtca ggagttcaag accagcctgg ccaacatggt    1560
gaaaccccgt ctctacaaaa atacaaaaat tagccaggcg tgatggcagg tgcctgtaat    1620
cctagctact tggcaggcta acgcaggaga atcacttgac cgggagacag aggttgcagt    1680
gagctgagat cgtacctatt gcactccatc ctggatgaaa gagccagact ctgtctcaaa    1740
acaaacaaaa aagcgtgggg acttctgggg acagacaagg tgcctgttat atatttactc    1800
```

-continued

```
agtctttgcc ctgaatggtc tcagcttgag accatttcaa actggagaga agcaagccag    1860
ccaatagaat ggggtgattt acagggattt ctgtttactg tcaaatatt tctcatctgc     1920 actatgtttc catttgtggt cctgaaggaa attcttataa ctcaacattt gtctggtctt    1980
ataagtaaag acagctttaa aatctgttca ctttcaaa                            2018
```

<210> SEQ ID NO 4
<211> LENGTH: 260
<212> TYPE: PRT
<213> ORGANISM: Homo sapiens

<400> SEQUENCE: 4

```
Met Ala Lys Asp Asn Ser Thr Val Arg Cys Phe Gln Gly Leu Leu Ile
1               5                   10                  15

Phe Gly Asn Val Ile Ile Gly Cys Cys Gly Ile Ala Leu Thr Ala Glu
            20                  25                  30

Cys Ile Phe Phe Val Ser Asp Gln His Ser Leu Tyr Pro Leu Leu Glu
        35                  40                  45

Ala Thr Asp Asn Asp Asp Ile Tyr Gly Ala Ala Trp Ile Gly Ile Phe
    50                  55                  60

Val Gly Ile Cys Leu Phe Cys Leu Ser Val Leu Gly Ile Val Gly Ile
65                  70                  75                  80

Met Lys Ser Ser Arg Lys Ile Leu Leu Ala Tyr Phe Ile Leu Met Phe
                85                  90                  95

Ile Val Tyr Ala Phe Glu Val Ala Ser Cys Ile Thr Ala Ala Thr Gln
            100                 105                 110

Gln Asp Phe Phe Thr Pro Asn Leu Phe Leu Lys Gln Met Leu Glu Arg
        115                 120                 125

Tyr Gln Asn Asn Ser Pro Pro Asn Asn Asp Asp Gln Trp Lys Asn Asn
    130                 135                 140

Gly Val Thr Lys Thr Trp Asp Arg Leu Met Leu Gln Asp Asn Cys Cys
145                 150                 155                 160

Gly Val Asn Gly Pro Ser Asp Trp Gln Lys Tyr Thr Ser Ala Phe Arg
                165                 170                 175

Thr Glu Asn Asn Asp Ala Asp Tyr Pro Trp Pro Arg Gln Cys Cys Val
            180                 185                 190

Met Asn Asn Leu Lys Glu Pro Leu Asn Leu Glu Ala Cys Lys Leu Gly
        195                 200                 205

Val Pro Gly Phe Tyr His Asn Gln Gly Cys Tyr Glu Leu Ile Ser Gly
    210                 215                 220

Pro Met Asn Arg His Ala Trp Gly Val Ala Trp Phe Gly Phe Ala Ile
225                 230                 235                 240

Leu Cys Trp Thr Phe Trp Val Leu Leu Gly Thr Met Phe Tyr Trp Ser
                245                 250                 255

Arg Ile Glu Tyr
            260
```

<210> SEQ ID NO 5
<211> LENGTH: 932
<212> TYPE: DNA
<213> ORGANISM: Homo sapiens

<400> SEQUENCE: 5

```
gaaagcctgc cagcacctat tccacctccc agcccagcat ggcacccctg ctgcccatcc     60
ggaccttgcc cttgatcctg attctgctgg ctctgctgtc cccaggggct gcagacttca    120
acatctcaag cctctctggt ctgctgtccc ggcgctaac ggagagcctg ctggttgcct     180
```

```
tgcccccctg tcacctcaca ggaggcaatg ccacactgat ggtccggaga gccaatgaca      240
gcaaagtggt gacgtccagc tttgtggtgc ctccgtgccg tgggcgcagg gaactggtga      300
gtgtggtgga cagtggtgct ggcttcacag tcactcggct cagtgcatac caggtgacaa      360
acctcgtgcc aggaaccaaa ttctacattt cctaccagtg aagaagggga cagccactg      420 agtccagcag agagatccca atgtccacac tccctcgaag gaacatggaa tccattgggc      480
tgggtatggc ccgcacaggg ggcatggtgg tcatcacggt gctgctctct gtcgccatgt      540
tcctgctggt gctgggcttc atcattgccc tggcactggg ctcccgcaag taaggaggtc      600
tgcccggagc agcagcttct ccaggaagcc cagggcacca tccagctccc cagcccacct      660
gctcccaggc ccaggcctg tggctcccctt ggtgccctcg cctcctcctc ctgccctcct      720
ctcccctaga gccctctcct ccctctgtcc ctctccttgc ccccagtgcc tcaccttcca      780
acactccatt attcctctca ccccactcct gtcagagttg actttcctcc cattttacca      840 cttttaaacac cccataaca attcccccat ccttcagtga actaagtccc tataataaag      900
gctgaggctg catctgccaa aaaaaaaaaa aa                                   932

<210> SEQ ID NO 6
<211> LENGTH: 184
<212> TYPE: PRT
<213> ORGANISM: Homo sapiens

<400> SEQUENCE: 6

Met Ala Pro Leu Leu Pro Ile Arg Thr Leu Pro Leu Ile Leu Ile Leu
 1               5                  10                  15

Leu Ala Leu Leu Ser Pro Gly Ala Ala Asp Phe Asn Ile Ser Ser Leu
            20                  25                  30

Ser Gly Leu Leu Ser Pro Ala Leu Thr Glu Ser Leu Leu Val Ala Leu
        35                  40                  45

Pro Pro Cys His Leu Thr Gly Gly Asn Ala Thr Leu Met Val Arg Arg
    50                  55                  60

Ala Asn Asp Ser Lys Val Val Thr Ser Ser Phe Val Val Pro Pro Cys
65                  70                  75                  80

Arg Gly Arg Arg Glu Leu Val Ser Val Val Asp Ser Gly Ala Gly Phe
                85                  90                  95

Thr Val Thr Arg Leu Ser Ala Tyr Gln Val Thr Asn Leu Val Pro Gly
            100                 105                 110

Thr Lys Phe Tyr Ile Ser Tyr Leu Val Lys Lys Gly Thr Ala Thr Glu
        115                 120                 125

Ser Ser Arg Glu Ile Pro Met Ser Thr Leu Pro Arg Arg Asn Met Glu
    130                 135                 140

Ser Ile Gly Leu Gly Met Ala Arg Thr Gly Gly Met Val Val Ile Thr
145                 150                 155                 160

Val Leu Leu Ser Val Ala Met Phe Leu Leu Val Leu Gly Phe Ile Ile
                165                 170                 175

Ala Leu Ala Leu Gly Ser Arg Lys
            180

<210> SEQ ID NO 7
<211> LENGTH: 1059
<212> TYPE: DNA
<213> ORGANISM: Homo sapiens

<400> SEQUENCE: 7
ccgttccgcg ctctggcggc tcctcccggg cgatgcctcc gctctgggcc ctgctggccc       60
```

```
tcggctgcct gcggttcggc tcggctgtga acctgcagcc ccaactggcc agtgtgactt    120
tcgccaccaa caaccccaca cttaccactg tggccttgga aaagcctctc tgcatgtttg    180
acagcaaaga ggccctcact ggcacccacg aggtctacct gtatgtcctg gtcgactcag    240
ccatttccag gaatgcctca gtgcaagaca gcaccaacac cccactgggc tcaacgttcc    300
tacaaacaga gggtgggagg acaggtccct acaaagctgt ggcctttgac ctgatcccct    360
gcagtgacct gcccagcctg gatgccattg gggatgtgtc caaggcctca cagatcctga    420
atgcctacct ggtcagggtg ggtgccaacg ggacctgcct gtgggatccc aacttccagg    480
gcctctgtaa cgcacccctg tcggcagcca cggagtacag gttcaagtat gtcctggtca    540
atatgtccac gggcttggta gaggaccaga ccctgtggtc ggaccccatc cgcaccaacc    600
agctcacccc atactcgacg atcgacacgt ggccaggccg gcggagcgga ggcatgatcg    660
tcatcacttc catcctgggc tccctgccct ctttctact tgtgggtttt gctggcgcca    720
ttgccctcag cctcgtggac atggggagtt ctgatgggga acgactcac gactcccaaa    780 tcactcagga ggctgttccc aagtcgctgg gggcctcgga gtcttcctac acgtccgtga    840
accgggggcc gccactggac agggctgagg tgtattccag caagctccaa gactgagccc    900
agcaccaccc ctgggcagca gcatcctcct ctctggcctt gccccaggcc ctgcagcggt    960
ggttgtcaca ccctgacttc agggaaggtg aaacagggct gtccctcca actgcaggaa   1020 aacccttaat aaaatcttct gatgagttct aaaaaaaaa                        1059
```

```
<210> SEQ ID NO 8
<211> LENGTH: 287
<212> TYPE: PRT
<213> ORGANISM: Homo sapiens

<400> SEQUENCE: 8

Met Pro Pro Leu Trp Ala Leu Leu Ala Leu Gly Cys Leu Arg Phe Gly
  1               5                  10                  15

Ser Ala Val Asn Leu Gln Pro Gln Leu Ala Ser Val Thr Phe Ala Thr
                 20                  25                  30

Asn Asn Pro Thr Leu Thr Thr Val Ala Leu Glu Lys Pro Leu Cys Met
             35                  40                  45

Phe Asp Ser Lys Glu Ala Leu Thr Gly Thr His Glu Val Tyr Leu Tyr
     50                  55                  60

Val Leu Val Asp Ser Ala Ile Ser Arg Asn Ala Ser Val Gln Asp Ser
 65                  70                  75                  80

Thr Asn Thr Pro Leu Gly Ser Thr Phe Leu Gln Thr Glu Gly Gly Arg
                 85                  90                  95

Thr Gly Pro Tyr Lys Ala Val Ala Phe Asp Leu Ile Pro Cys Ser Asp
            100                 105                 110

Leu Pro Ser Leu Asp Ala Ile Gly Asp Val Ser Lys Ala Ser Gln Ile
        115                 120                 125

Leu Asn Ala Tyr Leu Val Arg Val Gly Ala Asn Gly Thr Cys Leu Trp
    130                 135                 140

Asp Pro Asn Phe Gln Gly Leu Cys Asn Ala Pro Leu Ser Ala Ala Thr
145                 150                 155                 160

Glu Tyr Arg Phe Lys Tyr Val Leu Val Asn Met Ser Thr Gly Leu Val
                165                 170                 175

Glu Asp Gln Thr Leu Trp Ser Asp Pro Ile Arg Thr Asn Gln Leu Thr
            180                 185                 190

Pro Tyr Ser Thr Ile Asp Thr Trp Pro Gly Arg Arg Ser Gly Gly Met
```

```
              195                 200                 205
Ile Val Ile Thr Ser Ile Leu Gly Ser Leu Pro Phe Phe Leu Leu Val
    210                 215                 220

Gly Phe Ala Gly Ala Ile Ala Leu Ser Leu Val Asp Met Gly Ser Ser
225                 230                 235                 240

Asp Gly Glu Thr Thr His Asp Ser Gln Ile Thr Gln Glu Ala Val Pro
                245                 250                 255

Lys Ser Leu Gly Ala Ser Glu Ser Ser Tyr Thr Ser Val Asn Arg Gly
            260                 265                 270

Pro Pro Leu Asp Arg Ala Glu Val Tyr Ser Ser Lys Leu Gln Asp
        275                 280                 285

<210> SEQ ID NO 9
<211> LENGTH: 976
<212> TYPE: DNA
<213> ORGANISM: Homo sapiens

<400> SEQUENCE: 9
ccgttccgcg ctctggcggc tcctcccggg cgatgcctcc gctctgggcc ctgctggccc      60
tcggctgcct gcggttcggc tcggctgtga acctgcagcc ccaactggcc agtgtgactt     120
tcgccaccaa caaccccaca cttaccactg tggccttgga aaagcctctc tgcatgtttg     180
acagcaaaga ggccctcact ggcacccacg aggtctacct gtatgtcctg gtcgactcag     240
ccatttccag gaatgcctca gtgcaagaca gcaccaacac cccactgggc tcaacgttcc     300
tacaaacaga gggtgggagg acaggtccct acaaagctgt ggcctttgac ctgatccccct     360 gcagtgacct gcccagcctg gatgccattg ggatgtgtc caaggcctca cagatcctga     420
atgcctacct ggtcagggtg ggtgccaacg ggacctgcct gtgggatccc aacttccagg     480
gcctctgtaa cgcacccctg tcggcagcca cggagtacag tcaccccata tcgacgatc     540 gacacgtggc caggccggcg gagcggaggc atgatcgtca tcacttccat cctgggctcc     600
ctgcccttct ttctacttgt gggttttgct ggcgccattg ccctcagcct cgtggacatg     660
gggagttctg atggggaaac gactcacgac tcccaaatca ctcaggaggc tgttcccaag     720
tcgctggggg cctcggagtc ttcctacacg tccgtgaacc gggggccgcc actggacagg     780
gctgaggtgt attccagcaa gctccaagac tgagcccagc caccccctg ggcagcagca     840 tcctcctctc tggccttgcc ccaggccctg cagcggtggt tgtcacaccc tgacttcagg     900
gaaggtgaaa cagggcttgt ccctccaact gcaggaaaac ccttaataaa atcttctgat     960
gagttctaaa aaaaaa                                                    976

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide PCR primer

<400> SEQUENCE: 10
atggcgtctg cggcagcagc                                                 20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide PCR primer
```

<400> SEQUENCE: 11
ggaggaggat gcggaggagt c                                    21

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide PCR primer

<400> SEQUENCE: 12
agctcctaca cccaccgtga                                      20

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide PCR primer

<400> SEQUENCE: 13
aagaggaggc gcttgccttc ag                                   22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide PCR primer

<400> SEQUENCE: 14
aggagagagc tggttccagc ac                                   22

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide PCR primer

<400> SEQUENCE: 15
tggcatcttg tatcacagca gca                                  23

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide PCR primer

<400> SEQUENCE: 16
ccagtagaac atggtaccca ggag                                 24

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide PCR primer

<400> SEQUENCE: 17
agcctgccag cacctattcc ac                                              22

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide PCR primer

<400> SEQUENCE: 18
cttcctggag aagctgctgc tc                                              22

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide PCR primer

<400> SEQUENCE: 19
ttccgcgctc tggcggctcc t                                               21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide PCR primer

<400> SEQUENCE: 20
aaggccagag aggaggatgc t                                               21

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide PCR primer

<400> SEQUENCE: 21
gaatgcctca gtgcaagaca gc                                              22

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide PCR primer

<400> SEQUENCE: 22
tggttggtgc ggatggggtc                                                 20

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide PCR primer

<400> SEQUENCE: 23
tcggcagcca cggagtacag tcac                                            24

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide PCR primer

<400> SEQUENCE: 24
ggatttggtc gtattgggcg cct                                              23

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide PCR primer

<400> SEQUENCE: 25
agtgagcttc ccgtctagct cag                                              23

<210> SEQ ID NO 26
<211> LENGTH: 212
<212> TYPE: PRT
<213> ORGANISM: Homo sapiens

<400> SEQUENCE: 26

Met Pro Pro Leu Trp Ala Leu Leu Ala Leu Gly Cys Leu Arg Phe Gly
 1               5                  10                  15

Ser Ala Val Asn Leu Gln Pro Gln Leu Ala Ser Val Thr Phe Ala Thr
            20                  25                  30

Asn Asn Pro Thr Leu Thr Thr Val Ala Leu Glu Lys Pro Leu Cys Met
        35                  40                  45

Phe Asp Ser Lys Glu Ala Leu Thr Gly Thr His Glu Val Tyr Leu Tyr
    50                  55                  60

Val Leu Val Asp Ser Ala Ile Ser Arg Asn Ala Ser Val Gln Asp Ser
65                  70                  75                  80

Thr Asn Thr Pro Leu Gly Ser Thr Phe Leu Gln Thr Glu Gly Gly Arg
                85                  90                  95

Thr Gly Pro Tyr Lys Ala Val Ala Phe Asp Leu Ile Pro Cys Ser Asp
            100                 105                 110

Leu Pro Ser Leu Asp Ala Ile Gly Asp Val Ser Lys Ala Ser Gln Ile
        115                 120                 125

Leu Asn Ala Tyr Leu Val Arg Val Gly Ala Asn Gly Thr Cys Leu Trp
    130                 135                 140

Asp Pro Asn Phe Gln Gly Leu Cys Asn Ala Pro Leu Ser Ala Ala Thr
145                 150                 155                 160

Glu Tyr Ser His Pro Ile Leu Asp Asp Arg His Val Ala Arg Pro Ala
                165                 170                 175

Glu Arg Arg His Asp Arg His His Phe His Pro Gly Leu Pro Ala Leu
            180                 185                 190

Leu Ser Thr Cys Gly Phe Cys Trp Arg His Cys Pro Gln Pro Arg Gly
        195                 200                 205

His Gly Glu Phe
    210

METHOD FOR DETECTING VESICOURETERAL REFLUX OR INTERSTITIAL CYSTITIS

TECHNICAL FIELD

The present invention relates to a method for detecting vesicoureteral reflux or interstitial cystitis, a diagnostic agent therefor, and a diagnostic kit therefor.

BACKGROUND ART

Vesicoureteral reflux (VUR) is a congenital disease, the incidence of which differs greatly according to race. It is reported that the incidence of VUR is observed in 10% or more of the fetuses of white people of U.S.A. and Europe, which is the highest level of incidence among all the races. Prognosis varies depending on a variety of factors such as the severity of VUR, complications with congenital renal hypoplasia, or occurrence of renal scars resulting from recurring urinary tract infection. When adequate medical treatment is not provided at an early stage, VUR often develops into renal dysfunction and then into renal failure at maturity. It has actually been reported that VUR is observed in approximately 20% of patients with advanced renal dysfunctions. The diagnosis of VUR requires voiding cystography that involves the insertion of a catheter into the urethra. Despite the seriousness of VUR, a simple diagnostic method that can be utilized for screening has not yet been established. Thus, almost every patient suspected of having VUR is required to undergo an invasive X-ray test under the present circumstances.

If VUR is diagnosed at an early stage, many patients who would eventually develop renal failure and have to receive long-term hemodialysis can be relieved by the provision of adequate medical treatment and management. This can result in conservation of medical resources on a global scale. Accordingly, development of a simple and non-invasive diagnostic method that can easily detect VUR in all newborn babies has been awaited.

Interstitial cystitis (IC) is a relatively common disease, to an extent that there are approximately 700,000 patients in U.S.A. (90% or more of the patients are females). The principal complaints of IC are a strong urgency of urination, an increased urinary frequency, and pain when the bladder is full. Although the severity thereof varies, the "quality of life" of the patients becomes significantly deteriorated. However, no effective therapeutic method has yet been developed. Diagnosis of IC has never been easy. It is a serious issue of concern that diagnosis of IC requires invasive tests, such as observation of mucosal petechial bleeding via cystoscopy and biopsy of bladder mucosa under anesthesia, in addition to a thorough inquiry and an urodynamics. Many factors, such as mechanical irritation, allergy, immune responses, neurovascular problems, or urinary tract infection, are considered to be associated with IC. However, there is no conclusive evidence regarding any such factors, and a simple and non-invasive method for diagnosing IC has not yet been developed.

Uroplakins (UPs) are membrane proteins that are expressed specifically in urothelial cells (of the mucous membrane of the urethra, the bladder, the ureter or the renal pelvis), and 4 types of constitutive proteins have been identified. They are the 27-kDa Ia (UPIa), the 28-kDa Ib (UPIb), the 15-kDa II (UPII), and the 47-kDa III (UPIII) types. These 4 types of protein families form plaques on the uppermost urothelial layer. The uroplakin family is considered to function to stabilize the urothelial surface or as a permeability barrier, although the detailed physiology thereof has not yet been elucidated. In the Japanese Journal of Cancer Research, 89: 879, 1998, cloning of the human UPIII gene was reported. In the Japanese Journal of Cancer Research, 93: 523, 2002, a polyclonal antibody specific for UPIa was reported, and the clinical utility thereof as a histological marker of urinary tract transitional epithelial carcinoma (bladder carcinoma, ureteral carcinoma, or renal pelvic carcinoma) was suggested.

In recent years, a report has been made in which a uroplakin III (UPIII) gene knockout mouse, which had been prenatally subjected to genetic engineering so as not to allow the target protein to express its functions, developed bilateral VUR (Journal of Cell Biology, 151: 961, 2000). In contrast, it was also reported that "gene mutation was not detected" as a result of UPIII gene analysis, which targeted patients with familial VUR (Journal of Urology, 171: 931-2, 2004). Accordingly, causes for VUR or IC have not yet been elucidated, and no screening method that can be employed has yet been known.

DISCLOSURE OF THE INVENTION

The objects of the present invention are to discover a novel marker of vesicoureteral reflux or interstitial cystitis and to provide a simple and non-invasive method for detecting vesicoureteral reflux or interstitial cystitis.

The present inventors have conducted concentrated studies in order to attain the above objects. As a result, they discovered that expression of uroplakin, which is a membrane protein expressed specifically in urothelial cells, is enhanced in the epithelial cells of a patient with vesicoureteral reflux or interstitial cystitis. This has led to the completion of the present invention.

More specifically, the present invention includes the following.

(1) A method for detecting vesicoureteral reflux or interstitial cystitis comprising detecting uroplakin expression in a sample obtained from a subject.

(2) The method according to (1), wherein the uroplakin is uroplakin III.

(3) The method according to (1) or (2), wherein uroplakin expression is detected by detecting a polynucleotide that encodes uroplakin in a sample obtained from a subject.

(4) The method according to any of (1) to (3), wherein uroplakin expression is detected using an oligonucleotide primer comprising at least 15 continuous nucleotides for specifically amplifying a polynucleotide that encodes uroplakin or a polynucleotide probe comprising at least 15 continuous nucleotides specifically hybridizing with a polynucleotide that encodes uroplakin.

(5) The method according to any of (1) to (4), wherein the sample obtained from a subject is urine.

(6) A diagnostic agent for vesicoureteral reflux or interstitial cystitis comprising an antibody that specifically binds to uroplakin or a fragment thereof.

(7) A diagnostic agent for vesicoureteral reflux or interstitial cystitis comprising an oligonucleotide primer comprising at least 15 continuous nucleotides for specifically amplifying a polynucleotide that encodes uroplakin or a polynucleotide probe comprising at least 15 continuous nucleotides specifically hybridizing with a polynucleotide that encodes uroplakin.

(8) A diagnostic kit for vesicoureteral reflux or interstitial cystitis comprising the diagnostic agent according to (6) or (7).

(9) The following DNA (a) or (b):
(a) DNA comprising the nucleotide sequence as shown in SEQ ID NO: 9; or (b) DNA hybridizing under stringent conditions with DNA that consists of a nucleotide sequence complementary to DNA consisting of all or part of the nucleotide sequence as shown in SEQ ID NO: 9 and encoding a polypeptide encoded by a polynucleotide consisting of the nucleotide sequence, the expression of which is enhanced in a patient with vesicoureteral reflux or interstitial cystitis.

The present invention provides a novel and effective marker of vesicoureteral reflux or interstitial cystitis.

PREFERRED EMBODIMENTS OF THE INVENTION

Figure 1:
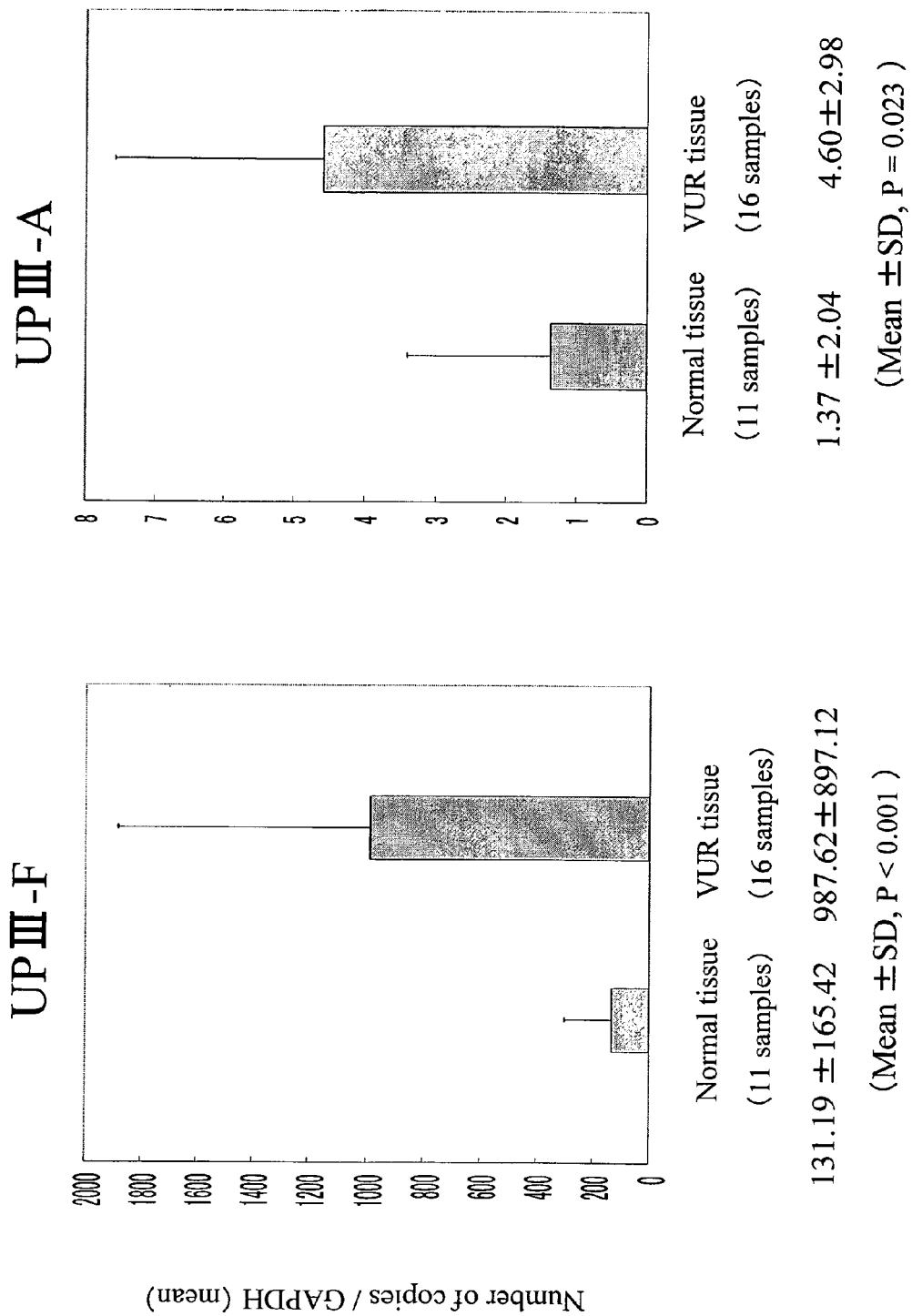
FIG. 1 shows the expression level of uroplakin III mRNA in tissues.

The present inventors used the urothelial tissue samples obtained from patients with VUR, patients with IC, and controls to compare the expression levels of messenger RNA (mRNA) to analyze the expression levels of the uroplakin genes. As a result, the levels of uroplakin mRNA expression were found to be enhanced in the urothelial tissue samples obtained from patients with VUR and patients with IC. Further, the present inventors discovered a novel selective splicing variant of uroplakin III (UPIII-A) with 83 residues in the translation domain deleted from a full-length uroplakin III mRNA (UPIII-F) consisting of 1,059 residues during the experiment using uroplakin III. They also confirmed that overexpression of UPIII-A was observed in the tissues obtained from patients with VUR.

Uroplakin

In the present invention, the term "uroplakin (UP)" refers to a membrane protein that is expressed specifically in urothelial cells (of the mucous membrane of the urethra, the bladder, the ureter or the renal pelvis). UP includes Ia (UPIa), Ib (UPIb), II (UPII), and III (UPIII). The nucleotide sequences of polynucleotides that encode uroplakin Ia, Ib, II, and III are registered with GenBank under the accession numbers of, for example, NM_007000 (SEQ ID NO: 1), AB002155 (SEQ ID NO: 3), NM_006760 (SEQ ID NO: 5), and NM_006953 (SEQ ID NO: 7). The amino acid sequences of uroplakin Ia, Ib, II, and III are registered with GenBank under the accession numbers of, for example, NP_008931 (SEQ ID NO: 2), BAA88878 (SEQ ID NO: 4), NP_006751 (SEQ ID NO: 6), and NP_008884 (SEQ ID NO: 8). In the nucleotide sequence of a polynucleotide that encodes uroplakin III as shown in SEQ ID NO: 7, the region between residue 241 and residue 520 corresponds to the third exon (hereafter it may be referred to as "exon 3"), the region between residue 521 and residue 603 corresponds to the fourth exon (hereafter it may be referred to as "exon 4"), and the region between residue 604 and residue 736 corresponds to the fifth exon (hereafter it may be referred to as "exon 5"). The nucleotide sequence of a polynucleotide that encodes a novel selective splicing variant of uroplakin III (UPIII-A) lacking exon 4 is shown in SEQ ID NO: 9.

In the present invention, an example of a polynucleotide that encodes uroplakin is a polynucleotide that is functionally equivalent to a polynucleotide represented by any of the aforementioned nucleotide sequences (SEQ ID NO: 1, 3, 5, 7, and 9). The term "functionally equivalent" used herein means that a polypeptide encoded by the target polynucleotide has biological and biochemical functions equivalent to those of a polypeptide encoded by a polynucleotide consisting of each of the aforementioned nucleotide sequences.

An example of another method that is well known in the art for preparing a polynucleotide that encodes a polypeptide that is functionally equivalent to a given polypeptide is a method that employs hybridization (Sambrook, J. et al., Molecular Cloning: 2nd ed., 9.47-9.58, Cold Spring Harbor Lab. Press, 1989).

In the present invention, examples of a polynucleotide that encodes uroplakin include a polynucleotide that comprises each of the aforementioned nucleotide sequences and a polynucleotide that hybridizes under stringent conditions with a polynucleotide consisting of a nucleotide sequence complementary to a polynucleotide consisting of all or part of the nucleotide sequence and that encodes a polypeptide, the expression of which is enhanced in a patient with VUR or IC. In this description, polynucleotides include DNA and RNA. The term "part of the sequence" refers to a nucleotide sequence of a polynucleotide that comprises part of the nucleotide sequence of each of the aforementioned polynucleotides. Such nucleotide sequence is long enough to hybridize under stringent conditions. For example, such sequence comprises at least 50 nucleotides, preferably at least 100 nucleotides, and more preferably at least 200 nucleotides.

The term "stringent conditions" used herein refers to conditions where a specific hybrid is formed but a non-specific hybrid is not formed. Specifically, hybridization of a polynucleotide having high homology (80% or higher, preferably 90% or higher, and more preferably 95% or higher homology) to each of the aforementioned polynucleotides is occurred under such conditions. Low stringent conditions constitute an example of hybridization conditions. Under low stringent conditions, for example, a step of washing following hybridization is carried out at 42° C. in 5×SSC and 0.1% SDS, and preferably at 50° C. in 5×SSC and 0.1% SDS. High stringent conditions constitute an example of more preferable hybridization conditions. Under high stringent conditions, for example, hybridization is carried out at 65° C. in 0.1×SSC and 0.1% SDS. Under such conditions, a polynucleotide having higher homology can be effectively obtained, as the temperature is raised. However, several elements such as temperature or salt concentration could affect the hybridization stringency. A person skilled in the art can adequately select such elements to realize an equivalent level of stringency.

Also, polynucleotides that are functionally equivalent to each of the aforementioned polynucleotides can be isolated by the gene amplification technique that utilizes a primer synthesized based on nucleotide sequence information, such as the polymerase chain reaction (PCR) method.

The functionally equivalent polynucleotide that is isolated by the hybridization or gene amplification technique generally exhibits high homology at the amino acid sequence level. The term "high homology" refers to generally 50% or higher identity, preferably 75% or higher identity, more preferably 85% or higher identity, and further preferably 95% or higher identity, at the amino acid level.

Identity of amino acid sequences or nucleotide sequences can be determined via the BLAST algorithm of Karlin and Altschul (Proc. Natl. Acad. Sci. U.S.A., 90: 5873-5877, 1993). Based on this algorithm, programs referred to as BLASTN and BLASTX have been developed (Altschul et al., J. Mol. Biol. 215: 403-410, 1990). Details of these analytical techniques are known (http://www.ncbi.nlm.nih.gov.).

Detection of Uroplakin Expression in Sample

The detection method according to the present invention comprises detection of expression of at least one uroplakin selected from among uroplakin Ia, uroplakin Ib, uroplakin II, and uroplakin III. Preferably, such method at least detects the expression of uroplakin III.

The method of detecting uroplakin expression in a sample obtained from a subject according to the present invention includes a method of detecting uroplakin polypeptide in a sample obtained from a subject and a method of detecting RNA that encodes uroplakin in a sample obtained from a subject. Detection of RNA that encodes uroplakin includes detection of cDNA or cRNA converted from such RNA.

1. Detection of Uroplakin Polypeptide

Examples of a method of detecting uroplakin polypeptide in a sample include methods known in the art, such as enzyme-linked immunosorbent assay (ELISA), dual monoclonal antibody sandwich immunoassay (U.S. Pat. No. 4,376, 110), monoclonal-polyclonal antibody sandwich assay (Wide et al., Kirkham and Hunter (ed.), "Radioimmunoassay," E. and S. Livingstone, Edinburgh, 1970), immunofluorescence, Western blotting, dot blotting, the immunoprecipitation method, protein chip-based analysis (Protein, Nucleic Acid, And Enzyme, vol. 47, No. 5, 2002; Protein, Nucleic Acid, and Enzyme, vol. 47, No. 8, 2002), two dimensional electrophoresis, and SDS-polyacrylamide electrophoresis, although the methods of detection are not limited thereto.

Hereafter, a method for detecting uroplakin expression using an antibody that specifically binds to uroplakin or a fragment thereof is described in detail. Since an antibody that specifically reacts with uroplakin or a fragment thereof can bind to uroplakin expressed in the case of vesicoureteral reflux or interstitial cystitis, whether or not a sample is obtained from a patient or person at high risk can be determined by detecting the reaction of such antibody with uroplakin in the sample.

An antibody that specifically reacts with uroplakin or a fragment thereof is a polyclonal or monoclonal antibody, which can bind to an epitope of the uroplakin. The globulin type of the antibody of the present invention is not particularly limited as long as the antibody has the aforementioned features. Any of IgG, IgM, IgA, IgE, or IgD antibodies may be employed, with IgG and IgM antibodies being preferable. The monoclonal antibody of the present invention includes a "chimeric" antibody (immunoglobulin) wherein some portion of the heavy chain and/or the light chain is derived from a specific species or specific antibody class or subclass and the remaining part thereof is derived from a different species or a different antibody class or subclass and an antibody fragment such as an Fab, F(ab')$_2$, or Fv fragment, as long as it has desired biological activity (U.S. Pat. No. 4,816,567).

When producing the antibody of the present invention, a polypeptide as an immunogen (antigen) is prepared. Uroplakin or a fragment thereof is used as an immunogen polypeptide. The amino acid sequence of uroplakin that can be used as an immunogen in the present invention and the cDNA sequence that encodes the aforementioned polypeptide have been disclosed as described above. Accordingly, uroplakin or a fragment thereof that is used as an immunogen can be synthesized based on the disclosed amino acid sequence information via a conventional technique, such as solid-phase peptide synthesis. An example of a fragment of uroplakin is a partial peptide consisting of at least 6, preferably 6 to 500, and more preferably 8 to 50 amino acid residues of uroplakin. When an uroplakin fragment is used as an immunogen, it is preferably ligated to a carrier protein such as KLH or BSA.

Alternatively, a conventional gene recombination technique can be employed to produce uroplakin based on the information of cDNA that encodes uroplakin. Hereafter, production of uroplakin via a recombination technique is described.

A recombinant vector for uroplakin production can be obtained by ligating the disclosed cDNA sequence to an adequate vector. A transformant can be obtained by introducing the recombinant vector for uroplakin production into a host, so that uroplakin can be expressed therein.

Phage or plasmid vectors that are capable of autonomous replication in host microorganisms are used. Examples of plasmid vectors include: plasmids derived from *Escherichia coli* (e.g., pET21a, pGEX4T, pUC118, pUC119, pUC18, and pUC19); plasmids derived from *Bacillus subtilis* (e.g., pUB 110 and pTP5); and plasmids derived from yeast (e.g., YEp13, YEp24, and YCp50). Examples of phage vectors include λ phage (e.g., λgt11 and λZAP). Further, animal virus vectors such as vaccinia virus vectors and insect virus vectors such as baculovirus vectors can also be used.

Uroplakin cDNA can be ligated to and inserted into a vector in the following manner. Purified DNA is first cleaved with an adequate restriction enzyme, and the cleavage fragment is then inserted into a restriction or multicloning site of an adequate vector DNA.

According to need, a cis element such as an enhancer, a splicing signal, a polyA addition signal, a selection marker, or a ribosome binding sequence (SD sequence) can be ligated to a recombinant vector for uroplakin production that is used in mammalian cells, in addition to a promoter and uroplakin cDNA.

A DNA fragment is ligated to a vector fragment using conventional DNA ligase. The DNA fragment is then annealed to the vector fragment, followed by ligation. Thus, a recombinant vector for uroplakin production is prepared.

Host cells to be used for transformation are not particularly limited as long as uroplakin can be expressed therein. Examples thereof include: bacteria such as *Escherichia coli* and *Bacillus subtilis*; yeast; animal cells such as COS cells and CHO cells; and insect cells.

When a bacterial host cell is used, for example, a recombinant vector for uroplakin production is preferably capable of autonomous replication in the bacteria, and it is preferably composed of a promoter, a ribosome binding sequence, uroplakin DNA, and a transcription termination sequence. Also, it may comprise a gene that regulates a promoter. An example of an *Escherichia coli* host cell is *Escherichia coli* BRL. An example of a *Bacillus subtilis* host cell is *Bacillus subtilis*. Any promoter can be used as long as it can express uroplakin in a host such as *Escherichia coli*. A recombinant vector can be introduced into bacteria via any method for introducing DNA into bacteria. Examples thereof include a method that involves the use of calcium ions and electroporation.

When a yeast, animal cell, or insect cell host is used, uroplakin can also be produced in accordance with a technique known in the art.

The uroplakin that is used as an immunogen in the present invention can be obtained by culturing the transformant prepared above and recovering uroplakin from the culture product. The term "culture product(s)" refers to any of culture supernatants, cultured cells, cultured bacteria, or disrupted cells or bacteria. The transformant is cultured in a medium in accordance with a common technique for culturing of host cells.

As a medium for culturing the transformant obtained from a microorganism host such as *E. coli* or yeast, either a natural or synthetic medium may be used as long as it contains carbon sources, nitrogen sources, and inorganic salts assimilable by the microorganism and is capable of efficiently culturing the transformant.

Usually, culture is carried out under aerobic conditions such as shake culture or aeration agitation culture at 37° C. for 6 to 24 hours. During the culture, a pH is maintained at around a neutral level. The pH can be adjusted with an inorganic or organic acid, an alkali solution, or the like. During the culture, an antibiotic such as ampicillin or tetracycline may be added to the medium, if necessary.

When uroplakin is produced in bacteria or cells, a protein is extracted by disrupting bacteria or cells after the completion of culturing. When uroplakin is produced outside the bacteria or cells, the culture solution is used in that state, or bacteria or cells are removed by centrifugation or other means. Thereafter, general biochemical techniques for protein isolation and purification, such as ammonium sulfate precipitation, gel chromatography, ion exchange chromatography, or affinity chromatography, may be performed alone or in adequate combinations. Thus, uroplakin can be isolated and purified from the culture product.

Whether or not uroplakin has been obtained can be confirmed via SDS-polyacrylamide gel electrophoresis or other means.

The recombinant uroplakin that can be obtained by the aforementioned method includes a fusion protein with any other types of proteins. Examples thereof include fusion proteins with glutathione-5-transferase (GST) and green fluorescent protein (GFP). In some cases, peptides that were expressed in the transformed cells are translated and are then subjected to various modifications in the cells. Thus, modified peptides can also be used as uroplakins. Examples of such post-translational modifications include elimination of an N-terminal methionine, N-terminal acetylation, glycosylation, limited degradation by an intracellular protease, myristoylation, isoprenylation, and phosphorylation.

Subsequently, the obtained protein is dissolved in a buffer to prepare the immunogen. According to need, an adjuvant may be added for effective immunization. Examples of such adjuvant include commercially available complete Freund's adjuvant and incomplete Freund's adjuvant, and either thereof can be employed.

A monoclonal antibody may be produced by, for example, the hybridoma technique (Kohler and Milstein, Nature, 1975, 256: 495) or the recombination technique (U.S. Pat. No. 4,816,567). A monoclonal antibody may also be isolated from the phage antibody library. For example, a monoclonal antibody can be produced in the following manner.

i) Immunization and Sampling of Antibody-Producing Cells

The thus-obtained immunogen is administered to a mammalian animal such as a rat, mouse (e.g., a BALB/c inbred mouse), or rabbit. An immunogen dosage is adequately determined in accordance with the type of animal to be immunized, the route of administration, or other conditions. Such dosage is approximately 50 µg to 200 µg per animal. Immunization is primarily carried out by injecting the immunogen intravenously, hypodermically, or intraperitoneally. The intervals of immunization are not particularly limited. Additional immunization is carried out 2 to 6 times, and preferably 3 or 4 times, at intervals of several days to several weeks, and preferably intervals of 1 to 4 weeks, after the initial immunization. After the initial immunization, the antibody titer in the serum of the immunized animal is repeatedly measured via enzyme-linked immunosorbent assay (ELISA) or other means. When the antibody titer reached a plateau, the immunogen is injected intravenously or intraperitoneally as the final immunization. The antibody-producing cells are collected 2 to 5 days, and preferably 3 days, after the final immunization. Examples of antibody-producing cells include spleen cells, lymph node cells, and peripheral blood cells, with spleen cells or local lymph node cells being preferable.

ii) Cell Fusion

In order to obtain hybridomas, the antibody-producing cells thus obtained from the immunized animals are subjected to cell fusion with myeloma cells.

Commonly available established cells from animals such as mice can be employed as myeloma cells to be fused with the antibody-producing cells. Preferably, the myeloma cell line to be employed has drug selectivity, and such myeloma cells can survive in an HAT selective medium (containing hypoxanthine, aminopterin, and thymidine) only when fused with antibody-producing cells. The established cell line is preferably derived from an animal of the same species as the animal to be immunized. Specific examples of myeloma cells include hypoxanthine-guanine-phosphoribosyl transferase (HGPRT) deficient cells derived from the BALB/c mouse, such as the P3×63-Ag.8 strain, the P3×63-Ag.8.U1 strain, the P3/NSI/1-Ag4-1 strain, the P3x63Ag8.653 strain, and the Sp2/0-Ag14 strain.

Subsequently, the myeloma cells are subjected to cell fusion with the antibody-producing cells. Cell fusion is carried out by mixing the antibody-producing cells with the myeloma cells at a proportion of approximately 1:1 to 20:1 in a medium for animal cell culturing, such as serum-free DMEM or RPMI-1640 medium, in the presence of a cell fusion accelerator. As a cell fusion accelerator, for example, about 10% to 80% polyethylene glycol having an average molecular weight of 1,500 to 4,000 daltons can be used. An adjuvant such as dimethyl sulfoxide may occasionally be used in order to enhance the fusion efficiency. Further, antibody-producing cells can be fused with myeloma cells using a commercialized apparatus for cell fusion that utilizes electrical stimulation (e.g., electroporation).

iii) Selection and Cloning of Hybridomas

The hybridomas of interest are selected from the fused cells. Hybridoma selection is carried out as follows. A cell suspension is adequately diluted with, for example, RPMI-1640 medium containing fetal bovine serum. The resulting dilution is sowed on a microtiter plate at approximately $2 \times 10^5$ cells/well, a selection medium is added to each well, the selection medium is adequately exchanged with fresh selection medium thereafter, and culturing is conducted. Culture temperature is 20° C. to 40° C., and preferably approximately 37° C. When the myeloma cells are HGPRT deficient or thymidine kinase (TK) deficient, hybridomas of cells capable of antibody production and myeloma cells can be selectively cultured and proliferated with the use of a selection medium containing hypoxanthine, aminopterin, and thymidine (HAT medium). As a result, cells that begin to grow approximately 14 days after the initiation of culture in a selection medium can be obtained as hybridomas.

Subsequently, the culture supernatant of the proliferated hybridomas is screened to inspect whether the antibodies of interest are present or not. Screening of hybridomas can be carried out in accordance with a conventional technique without particular limitation. For example, part of the culture supernatant of grown hybridomas included in a well is sampled and then subjected to enzyme immunoassay such as EIA or ELISA or radioimmunoassay (RIA).

The fused cells are cloned via limiting dilution or other means, and hybridomas that are monoclonal antibody-producing cells are finally established. The hybridomas of the present invention are stable during culturing in a basal medium such as RPMI-1640 or DMEM, and produce and secrete the monoclonal antibodies that specifically react with uroplakin derived from vesicoureteral reflux, as described below.

iv) Sampling of Monoclonal Antibodies

Monoclonal antibodies can be sampled from established hybridomas via conventional cell culturing techniques, generation of ascites fluid, or other means.

In the case of cell culturing techniques, hybridomas are cultured in a medium for animal cell culture such as RPMI-1640 medium containing 10% fetal bovine serum, MEM medium, or serum-free medium under general culture conditions (e.g., at 37° C. in 5% $CO_2$) for 2 to 10 days, and antibodies are obtained from the culture supernatant.

In the case of generation of ascites fluid, about $1 \times 10^7$ hybridomas are administered intraperitoneally into a mammalian animal of the same species as the animal from which the myeloma cells were derived, and a large quantity of hybridomas are allowed to proliferate. Ascites fluid or serum is sampled 1 to 2 weeks thereafter.

When antibody purification is required in the method of sampling antibodies, conventional techniques, such as salting out by ammonium sulfate, ion exchange chromatography, affinity chromatography, or gel chromatography, can be adequately selected or combined to obtain the purified monoclonal antibodies according to the present invention.

v) Sampling of Polyclonal Antibodies

When polyclonal antibodies are produced, animals are immunized as described above, the antibody titer is measured via enzyme immunoassay such as EIA or ELISA, radio immunoassay (RIA), or other means 6 to 60 days after the final immunization, the blood sampling is carried out on the day when the maximal antibody titer is obtained, and the antiserum is obtained. Thereafter, reactivity of the polyclonal antibodies in the antiserum is assayed via ELISA or other means.

When detection of vesicoureteral reflux or interstitial cystitis is intended using the antibodies against uroplakin to detect uroplakin expression in the sample obtained from the subject, whether or not the antigen polypeptides that bind to the antibodies against uroplakin or the labeled antibodies thereof are present is inspected, and the subject whose sample contains the antigen polypeptides is evaluated as a patient with vesicoureteral reflux or interstitial cystitis or as being at high risk thereof. Specifically, the antibodies or the labeled antibodies to be employed herein bind specifically to uroplakins that are expressed in vesicoureteral reflux or interstitial cystitis cells. Accordingly, a sample containing an antigen polypeptide that is bound to such antibodies can be determined to be a sample of a patient with vesicoureteral reflux or interstitial cystitis or a patient at high risk thereof. In such a case, binding of preferably at least 2, more preferably at least 5, further preferably at least 10, and most preferably 15 to 39 types of antibodies to uroplakin in the sample is evaluated.

In another embodiment, binding of antibodies to uroplakin is detected in a liquid phase system. For example, the labeled antibodies are brought into contact with the sample to allow such antibodies to bind to uroplakin, the conjugate is separated in the manner as described above, and the label signal is then detected in the same manner as described above.

In another method of detection in a liquid phase system, antibodies against uroplakin (i.e., primary antibodies) are brought into contact with the samples to allow the primary antibodies to bind to the antigen polypeptides. The labeled antibodies (i.e., secondary antibodies) are then allowed to bind to the resulting conjugate, and the label signal of the conjugate of these three substances is detected. Alternatively, non-labeled secondary antibodies may first be bound to the conjugate of antibodies and antigen polypeptides, and the labeling substance may be allowed to bind to such secondary antibodies, in order to intensify the signal. Labeling substances can be bound to such secondary antibodies by, for example, biotinylating the secondary antibodies and avidinylating the labeling substances. Alternatively, antibodies (i.e., tertiary antibodies) that recognize part of the region (e.g., the Fc region) of the secondary antibodies are labeled, and the tertiary antibodies may be bound to the secondary antibodies. Both primary and secondary antibodies may be monoclonal. Alternatively, either the primary or secondary antibodies may be polyclonal. Separation of the conjugate from the liquid phase and signal detection are carried out in the same manner as described above.

According to another embodiment, binding of antibodies to uroplakin is tested in a solid phase system. Such technique is preferable for detecting an extremely small amount of uroplakin and simplifying the procedures. In this technique, specifically, antibodies against uroplakin (i.e., primary antibodies) are immobilized on a solid phase (e.g., a resin plate, membrane, or beads), uroplakin is allowed to bind to such immobilized antibodies, the unbound peptides are removed by washing, the labeled antibodies (i.e., secondary antibodies) are allowed to bind to the conjugate of antibodies and uroplakin remaining on the plate, and the signal emitted from the secondary antibodies is then detected. This technique is a so-called "sandwich method" that is extensively employed as ELISA when an enzyme marker is used. Both primary and secondary antibodies may be monoclonal. Alternatively, either the primary or secondary antibodies may be polyclonal. Signal detection is carried out in the same manner as described above.

2. Detection of Uroplakin RNA

RNA that encodes uroplakin in the sample obtained from the subject can be detected by a method wherein uroplakin expression in the sample obtained from the subject is detected using an oligonucleotide primer comprising at least 15 continuous nucleotides for specifically amplifying the polynucleotide that encodes uroplakin or a polynucleotide probe comprising at least 15 continuous nucleotides that specifically hybridizes with the polynucleotide that encodes uroplakin.

The terms "polynucleotide" and "oligonucleotide" refer to molecules wherein phosphoric acid esters (ATP, GTP, CTP, UTP, dATP, dGTP, dCTP, or dTTP) of nucleosides comprising purine or pyrimidine bound to a sugar via a β-N-glycoside bond have been bound, and they include DNA and RNA.

The aforementioned primer or probe specifically binds to uroplakin mRNA that is expressed in the sample obtained from the subject or cDNA or cRNA synthesized from the mRNA. Accordingly, expression of polynucleotides that encode uroplakin in the sample, i.e., expression of uroplakin, can be detected using such primer or probe.

Any primer can be used as the primer of the present invention as long as it can amplify the part of the polynucleotide that encodes uroplakin. For example, detection of uroplakin expression includes detection of a novel selective splicing variant of uroplakin III (UPIII-A) with 83 residues in the translation domain deleted from a full-length uroplakin III mRNA (UPIII-F) consisting of 1,059 residues.

Primers and probes can be designed in accordance with techniques known in the art. The following points should be taken into consideration when designing primers and probes.

The sufficient length to allow exhibition of the substantial functions of the primer is generally 15 or more, preferably 16 to 50, and more preferably 20 to 30 nucleotides. The sufficient length to allow exhibition of the substantial functions of the probes is preferably 15 or more, more preferably 16 to 50, and further preferably 20 to 30 nucleotides.

It is preferable to confirm the melting temperature (Tm) of the primers and the probes when designing them. The "Tm" refers to a temperature at which 50% of a given polynucleotide chain forms a hybrid with the complementary chain thereof. In order for the template DNA or RNA to be double-stranded with primers or probes for annealing or hybridization, the annealing or hybridization temperature must be optimized. When such temperature is excessively reduced, nonspecific reactions disadvantageously take place. Accordingly, as high a temperature as possible is preferably maintained. This indicates that the Tm of the primers or probes to be designed is an important factor when performing amplification or hybridization. The Tm can be confirmed using known software for primer or probe design. Examples of software that can be used in the present invention include Oligo™ (National Bioscience Inc., U.S.A.) and GENETYX (Software Development Co., Ltd., Japan). Also, the Tm can be confirmed via manual calculation without the use of software. In such a case, formulae based on the nearest neighbor method, the Wallance method, the GC % method, or the like can be used. In the present invention, the average Tm is preferably between approximately 45° C. and 55° C.

An example of another condition of primers or probes used to carry out specific annealing or hybridization is GC content. Such condition is known in the art.

The primers and probes designed as described above can be produced in accordance with a conventional technique known in the art. Further, the primers or probes may contain a sequence other than a part that is to be annealed or hybridized. Examples include an additional sequence such as a tag sequence, as known in the art. The present invention includes sequences prepared by adding such additional sequences to the primers or probes.

Examples of an oligonucleotide primer for specifically amplifying a polynucleotide that encodes uroplakin I include: an oligonucleotide consisting of the nucleotide sequence comprising at least nucleotides 1 to 21 and at least 15 continuous nucleotides of the nucleotide sequence as shown in SEQ ID NO: 1 or a complementary sequence thereof; an oligonucleotide consisting of the nucleotide sequence comprising at least nucleotides 811 to 831 and at least 15 continuous nucleotides of the nucleotide sequence as shown in SEQ ID NO: 1 or a complementary sequence thereof; and an oligonucleotide consisting of the nucleotide sequence comprising at least nucleotides 337 to 356 and at least 15 continuous nucleotides of the nucleotide sequence as shown in SEQ ID NO: 1 or a complementary sequence thereof.

Examples of an oligonucleotide primer for specifically amplifying a polynucleotide that encodes uroplakin Ib include: an oligonucleotide consisting of the nucleotide sequence comprising at least nucleotides 7 to 28 and at least 15 continuous nucleotides of the nucleotide sequence as shown in SEQ ID NO: 3 or a complementary sequence thereof; an oligonucleotide consisting of the nucleotide sequence comprising at least nucleotides 880 to 901 and at least 15 continuous nucleotides of the nucleotide sequence as shown in SEQ ID NO: 3 or a complementary sequence thereof; an oligonucleotide consisting of the nucleotide sequence comprising at least nucleotides 355 to 377 and at least 15 continuous nucleotides of the nucleotide sequence as shown in SEQ ID NO: 3 or a complementary sequence thereof; and an oligonucleotide consisting of the nucleotide sequence comprising at least nucleotides 789 to 812 and at least 15 continuous nucleotides of the nucleotide sequence as shown in SEQ ID NO: 3 or a complementary sequence thereof.

Examples of an oligonucleotide primer for specifically amplifying a polynucleotide that encodes uroplakin II include: an oligonucleotide consisting of the nucleotide sequence comprising at least nucleotides 4 to 22 and at least 15 continuous nucleotides of the nucleotide sequence as shown in SEQ ID NO: 5 or a complementary sequence thereof; and an oligonucleotide consisting of the nucleotide sequence comprising at least nucleotides 607 to 628 and at least 15 continuous nucleotides of the nucleotide sequence as shown in SEQ ID NO: 5 or a complementary sequence thereof.

Examples of an oligonucleotide primer for specifically amplifying a polynucleotide that encodes uroplakin III include: an oligonucleotide consisting of the nucleotide sequence comprising at least nucleotides 4 to 24 and at least 15 continuous nucleotides of the nucleotide sequence as shown in SEQ ID NO: 7 or a complementary sequence thereof; an oligonucleotide consisting of the nucleotide sequence comprising at least nucleotides 251 to 272 and at least 15 continuous nucleotides of the nucleotide sequence as shown in SEQ ID NO: 7 or a complementary sequence thereof; and an oligonucleotide consisting of the nucleotide sequence comprising at least nucleotides 582 to 601 and at least 15 continuous nucleotides of the nucleotide sequence as shown in SEQ ID NO: 7 or a complementary sequence thereof.

Examples of an oligonucleotide primer for specifically amplifying a polynucleotide that encodes a splicing variant of uroplakin III include: an oligonucleotide comprising at least nucleotides 4 to 24 and consisting of the nucleotide sequence composed of at least 15 continuous nucleotides of the nucleotide sequence as shown in SEQ ID NO: 7 or a complementary sequence thereof; an oligonucleotide comprising at least nucleotides 920 to 940 and consisting of the nucleotide sequence composed of at least 15 continuous nucleotides of the nucleotide sequence as shown in SEQ ID NO: 7 or a complementary sequence thereof; and an oligonucleotide comprising at least nucleotides 501 to 520 and nucleotides 604 to 607 and consisting of the nucleotide sequence composed of at least 15 continuous nucleotides of the nucleotide sequence as shown in SEQ ID NO: 7 or a complementary sequence thereof.

Uroplakin expression in the sample obtained from the subject is detected using the primers and/or probes in amplification or hybridization and detecting the products of amplification or hybridization.

When diagnosis of vesicoureteral reflux is intended, urine or bladder epithelial tissue samples are employed. When diagnosis of interstitial cystitis is intended, urine or bladder epithelial tissue samples are employed. The diagnostic method of the present invention can employ urine samples or the like, and thus, simple and non-invasive diagnosis can be performed.

When amplification or hybridization is carried out, a polynucleotide analyte is generally prepared from a sample obtained from the subject. The polynucleotide analyte may be a polynucleotide DNA or RNA. DNA or RNA can be adequately extracted via a method known in the art. For example, DNA can be extracted via phenol extraction, ethanol precipitation, or a method that involves the use of glass beads. RNA can be extracted via, for example, guanidine/cesium chloride ultracentrifugation, the hot phenol method, or the guanidinium thiocyanate-phenol-chloroform extraction (AGPC) method. Amplification and/or hybridization described below is carried out using the sample or polynucleotide analyte prepared as described above.

Preferably, the extracted RNA is further purified and then used as mRNA. The method of purification is not particularly limited. Since many mRNAs that are present in the cytoplams of the eukaryotic cells have poly (A) sequences on their 3' terminuses, for example, purification can be carried out with the utilization of such features in the following manner. At the outset, a biotinylated oligo (dT) probe is added to the extracted total RNA in order to allow poly (A)$^+$ RNA to adsorb thereto. Subsequently, paramagnetic particulate carriers having streptoavidin immobilized thereon are added, and a biotin-streptoavidin bond is utilized to trap poly (A)$^+$ RNA. After the washing procedure, poly (A)$^+$ RNA is eluted from the oligo (dT) probe at the end. Alternatively, purification can be carried out using an oligo (dT) cellulose column to adsorb poly (A)$^+$ RNA, followed by elution. The eluted poly (A)$^+$ RNA may be further fractionated via sucrose density gradient centrifugation or other means.

Amplification can be carried out using primers and the polynucleotide analyte as a template, and specific amplification is then detected. Thus, uroplakin expression in the sample can be detected.

A method of amplification is not particularly limited. An example thereof is a conventional method that utilizes the principle of the polymerase chain reaction (PCR). Specific examples thereof include loop-mediated isothermal amplification (LAMP), isothermal and chimeric primer-initiated amplification of nucleic acids (ICAN), rolling circle amplification (RCA), ligase chain reaction (LCR), strand displacement amplification (SDA), RT-PCR, and real-time PCR. Amplification is carried out until the amplification product becomes detectable.

In PCR, for example, DNA, which is a polynucleotide analyte, is used as a template and the nucleotide sequence between a primer pair are synthesized with the use of DNA polymerase. An amplified fragment can be exponentially amplified by repeating a cycle of denaturing, annealing, and synthesis by PCR. A person skilled in the art can easily determine the optimal conditions for PCR.

In the case of RT-PCR, RNA, which is a polynucleotide analyte, is employed as a template to first prepare cDNA by reverse transcriptase reactions, and PCR is then carried out using the prepared cDNA as a template and a primer pair.

Quantitative detection can be realized by adopting quantitative PCR such as competitive PCR or real-time PCR as a means of amplification. Real-time PCR (TaqMan PCR) employs an oligonucleotide probe that is labeled at the 5' terminus with a fluorescent dye (reporter) and at the 3' terminus with a fluorescent dye (quencher) and that hybridizes with a given region of the target gene. In a normal state, reporter fluorescence of the probe is inhibited by the quencher. This fluorescent probe is completely hybridized with the target gene, and PCR is carried out from the outside thereof using Taq DNA polymerase in that state. As elongation using the Taq DNA polymerase advances, the fluorescent probe is hydrolyzed from 5'-terminus by the exonuclease activity, a reporter dye is released, and fluorescence is emitted. In real-time PCR, the intensity of this fluorescence is monitored in real time to quantify the initial amount of template DNA.

Whether or not specific amplification took place after the amplification can be detected by a conventional technique, wherein the amplification product can be specifically recognized. For example, whether or not an amplification fragment of a given size is amplified can be determined via agarose gel electrophoresis or other means to detect specific amplification.

Alternatively, a label, such as a radioactive isotope, a fluorescent substance, or a luminous substance, is allowed to act on dNTP incorporated during amplification, and such label can be detected. Examples of radioactive isotopes that can be used include $^{32}$P, $^{125}$I, and $^{35}$S. Examples of fluorescent substances that can be used include fluorescein (FITC), sulforhodamine (SR), and tetramethylrhodamine (TRITC). An example of a luminous substance that can be used is luciferin.

The types of labels, the method for introducing the labels, and other conditions are not particularly limited, and any conventional means can be employed. For example, a label can be introduced by the random prime method, which involves the use of a radioactive isotope.

The amplification product having labeled dNTP incorporated therein can be observed via any of the aforementioned methods for detecting the label known in the art. When a radioactive isotope is used as a label, for example, the radioactivity can be measured using a liquid scintillation counter or a γ-counter. When a fluorescent substance is employed as a label, such fluorescence can be detected using a fluorescence microscope, a fluorescent plate reader, or the like.

When specific amplification is detected as described above, it indicates the expression of a polynucleotide that encodes uroplakin in the sample, i.e., the expression of uroplakin. Thus, a subject whose sample contains uroplakin expressed therein is evaluated as a patient with vesicoureteral reflux or interstitial cystitis or as being at high risk thereof.

Alternatively, using the probes, hybridization of samples or polynucleotide analytes to the probes can be carried out, and specific binding (hybrid formation) can be detected to detect uroplakin expression.

Hybridization must be carried out under stringent conditions, where a probe specifically and selectively binds only to a polynucleotide derived from uroplakin. Such stringent conditions are known in the art and are not particularly limited. Under stringent conditions, for example, sodium concentration is 10 mM to 300 mM, and preferably 20 mM to 100 mM, and the temperature is 25° C. to 70° C., and preferably 42° C. to 55° C.

When hybridization is carried out, an adequate label, such as a fluorescent label (e.g., fluorescein or rhodamine), a radioactive label (e.g., $^{32}$P), an enzyme label (e.g., alkaline phosphatase or horseradish peroxidase), or a biotin label, can be applied to a probe. Accordingly, the diagnostic kit of the present invention described below includes a probe to which such label has been applied.

Detection that involves the use of a labeled probe comprises a procedure wherein a sample or a polynucleotide analyte prepared therefrom is brought into contact with a probe, so that hybridization can be carried out. The phrase "so that hybridization can be carried out" means that such detection is carried out in an environment (i.e., temperature or sodium concentration) where specific binding takes place under the aforementioned stringent conditions. Specifically, a sample or a polynucleotide analyte is immobilized on an adequate solid phase such as a glass slide, membrane, or microtiter plate, and the labeled probes are applied thereto.

Hybridization is then carried out by bringing the probes into contact with the samples or polynucleotide analytes, the probes that did not hybridize with the samples or polynucleotide analytes are removed, and labels of the probes that hybridized with the samples or polynucleotide analytes are then detected. When labels are detected, this indicates the uroplakin expression in the samples. Accordingly, a subject whose sample contains uroplakin expressed therein is evaluated as a patient with vesicoureteral reflux or interstitial cystitis or as being at high risk thereof.

Also, quantitative detection can be carried out by employing label density as an indicator. Examples of detection methods that employ labeled probes include Southern hybridization, Northern hybridization, and fluorescence in situ hybridization (FISH).

A representative example of the standard in the detection method of the present invention described above is a method wherein a receiver operating characteristic (ROC) curve is prepared to set a cut off value (a threshold value of clinical conditions), and a subject who has a value higher than a given cut off value is evaluated as being a patient or as being at high risk. In the case of diagnosis of vesicoureteral reflux using a urine sample, for example, the optimal cut off value obtained from the ROC curve can be determined as being the value of a patient or a person at high risk when the sample contains 95 copies or more uroplakin mRNA per unit GAPDH, and 138 copies or more when 90% specificity is intended. Interstitial cystitis can also be evaluated in the same manner.

Examples of other detection methods include subtraction (Sive, H. L. and John, T. St., 1988, Nucleic Acids Research 16, 10937; Wang, Z., and Brown, D. D., 1991, Proc. Natl. Acad. Sci. U.S.A., 88, 11505-11509), differential display (Liang, P., and Pardee, A. B., 1992, Science 257, 967-971; Liang, P., Averboukh, L., Keyomarsi, K., Sager, R., and Pardee, A. B., 1992, Cancer Research 52, 6966-6968), differential hybridization (John, T. St., and Davis, R. W. Cell, 1979, 16, 443-452), and cross hybridization that involves the use of adequate probes ("Molecular Cloning: A Laboratory Manual," Maniatis, T., Fritsch, E. F., Sambrook, J., 1982, Cold Spring Harbor Laboratory Press).

Diagnostic Agent and Diagnostic Kit

The present invention also relates to a diagnostic agent for vesicoureteral reflux or interstitial cystitis. This diagnostic agent comprises, as a means of detecting uroplakin expression, at least one of the following: an antibody that binds specifically to uroplakin or a fragment thereof; an oligonucleotide primer that comprises at least 15 continuous nucleotides for specifically amplifying a polynucleotide that encodes uroplakin; and a polynucleotide probe that comprises at least 15 continuous nucleotides specifically hybridizing with a polynucleotide that encodes uroplakin.

Such diagnostic agent comprises, as an active ingredient, an oligonucleotide primer, a polynucleotide probe, or an antibody. In addition, the agent may comprise, for example, sterilized water, physiological saline, vegetable oil, a surfactant, fat, a solubilizing agent, a buffer, a protein stabilizer such as BSA or gelatin, or a preservative, according to need.

The present invention further relates to a diagnostic kit for vesicoureteral reflux or interstitial cystitis comprising the aforementioned diagnostic agent. A variety of kits are commercialized in accordance with different types of test materials. The diagnostic kit of the present invention can be composed of a variety of elements that are used for conventional kits, except for the use of the diagnostic agent for detecting uroplakin expression. In addition to the oligonucleotide primer, the polynucleotide probe, or the antibody for detecting uroplakin expression, the diagnostic kit of the present invention can comprise, for example, a labeled secondary antibody, a carrier, a washing buffer, a sample diluent, an enzyme substrate, a reaction stop solution, and a reference material.

EXAMPLES

Hereafter, the present invention is described in greater detail with reference to the following examples, although the technical scope of the present invention is not limited thereto.

Example 1

Expression Level of Uroplakin mRNA in Vesicoureteral Reflux (VUR)

Targets

In order to assay the expression levels of uroplakin mRNA in tissues obtained from patients with VUR, 20 bladder epithelial tissue samples of patients with VUR obtained through surgery at the Department of Urology at the Shiga University of Medical Science Hospital and 11 urothelial tissue samples of control patients (i.e., urologic patients with no obvious abnormalities in urinary tract transitional epithelia such as prostatic hyperplasia or prostate carcinoma) were used. Samples were preserved at −80° C. immediately after sampling. In order to assay the expression levels of uroplakin mRNA in exfoliated cells in urine, 18 urine specimens of patients with VUR obtained at the Department of Urology at the Shiga University of Medical Science Hospital and 20 urine specimens of control patients (i.e., 12 specimens obtained from urologic outpatients who have no obvious urinary tract abnormalities and 8 specimens obtained from healthy volunteers) were used. Basically, urine sampling was carried out via spontaneous micturition, and it was carried out via catheterization according to need. The urine samples were subjected to centrifugation to collect the exfoliated epithelium, washed with a buffer, and preserved at −80° C. immediately thereafter. Concerning the sampling of specimens, the use of the clinical materials in the research was thoroughly described in writing to the patients or proxies thereof, and consent was obtained from all of them.

Method (1) Sampling of mRNA and Synthesis of cDNA i) Tissue Specimen

Total RNAs were extracted from the preserved tissue specimens using TriZOL Reagent (Life Technologies, Inc.) in accordance with the protocol thereof, and the concentration was measured using a spectrophotometer. cDNAs were synthesized from 5 μg each of the extracted total RNA via reverse transcription using a random primer (Takara Biochemical) and SuperscriptII (Invitrogen), and the resultant was designated as a sample for the following experiment. The quality of cDNA synthesis was examined via RT-PCR using a primer specific for glyceraldehyde-3-phosphate dehydrogenase (GAPDH), and samples were then preserved at −20° C. before use.

ii) Urine Specimen

The urine samples were centrifuged at 1,500 rpm for 10 minutes to collect the exfoliated epithelium, washed two times in total with PBS buffer, and preserved at −80° C. immediately thereafter. Total RNAs were extracted using the TriZOL Reagent (Life Technologies, Inc.) in accordance with a conventional technique, cDNAs were synthesized from the total amount thereof in the same manner as with the tissue specimens, and the resulting cDNAs were preserved at −20° C. until they were used as experimental samples as follows.

(2) RT-PCR and Direct Sequencing of Full-Length UPIa, UPIb, UPII, and UPIII

The synthesized cDNAs were subjected to RT-PCR using LA taq (Takara Biochemical). RT-PCR was carried out in the following manner. cDNA (2 μl each) was placed into 20 μl of the reaction solution using the sense and antisense primers independently designed by the present inventors; i.e., primers used in RT-PCR are shown in Table 1. As described above, in the nucleotide sequence of a polynucleotide that encodes UPIII-F (complete) as shown in SEQ ID NO: 7, the region between nucleotides 241 and 520 corresponds to exon 3, the region between nucleotides 521 and 603 corresponds to exon 4, and the region between nucleotides 604 and 736 corresponds to exon 5.

TABLE 1

| mRNA | Primer type | Primer name | SEQ ID NO: | Sequence (5'→3') | Genbank accession No. (Translation domain) | Primer region (nr No.) |
|---|---|---|---|---|---|---|
| UPK 1a | Sense | UPK1A-S1 | 10 | atggcgtctgcggcagcagc | NM_007000 | 1-21 |
|  | Antisense | UPK1A-A1 | 11 | ggaggaggatgcggaggagtc | (1-777) | 811-831 |
|  | Sense | UPK1A-S2 | 12 | agctcctacacccaccgtga |  | 337-356 |
| UPK 1b | Sense | UPK1B-SI | 13 | aagaggaggcgcttgccttcag | AB002155 | 7-28 |
|  | Antisense | UPK1B-AI | 14 | aggagagagctggttccagcac | (48-830) | 880-901 |
|  | Sense | UPK1b-S2 | 15 | tggcatcttgtatcacagcagca |  | 355-377 |
|  | Antisense | UPK1b-A1 | 16 | ccagtagaacatggtacccaggag |  | 789-812 |
| UPK II | Sense | UPK2-SI | 17 | agcctgc cagcacctat tccac | NM_006760 | 4-22 |
|  | Antisense | UPK2-AI | 18 | cttcctggagaagctgctgctc | (39-593) | 607-628 |
| UPK III | Sense | UPK3-S1 | 19 | ttccgcgctctggcggctcct | NM_006953 | 4-24 |
|  | Antisense | UPK3-A2 | 20 | aaggccagagaggaggatgct | (33-896) | 920-940 |
|  | Sense | UPK3-SF | 21 | gaatgcctcagtgcaagacagc |  | 251-272 |
|  | Antisense | UPK3-A4 | 22 | tggttggtgcggatggggtc |  | 582-601 |
|  | Sense | UPK3-AL1 | 23 | tcggcagccacggagtacagtcac |  | 501-520 + 604-607 |
| GAPDH | Sense | GAPDH-S | 24 | ggatttggtcgtattgggcgcct | BC026907 | 66-88 |
|  | Antisense | GAPDH-A | 25 | agtgagcttcccgtctagctcag | (39-1046) | 703-725 |

UPK1A-S1 (SEQ ID NO: 10) and UPK1A-AI (SEQ ID NO: 11), UPK1B-SI (SEQ ID NO: 13) and UPK1B-AI (SEQ ID NO: 14), UPK2-SI (SEQ ID NO: 17) and UPK2-AI (SEQ ID NO: 18), and UPK3-S1 (SEQ ID NO: 19) and UPK3-A2 (SEQ ID NO: 20) (final concentration: 0.2 μmol/μl) for uroplakin Ia (UPIa), uroplakin Ib (UPIb), uroplakin II (UPII), and uroplakin III (UPIII), respectively. An amplification cycle of denaturation at 94° C. for 30 seconds, annealing at 62° C. for 30 seconds, and elongation at 72° C. for 1 minute was repeated 30 times. The PCR product was electrophoresed on 2% agarose gel to which ethidium bromide had been added, and the visualized bands were cleaved and then purified using the QIAquick Gel Extraction Kit (Qiagen). Direct sequencing was carried out on an ABI PRISM 310 DNA sequencer (Applied Biosystems) using the BigDye Terminator Cycle Sequencing Ready Reaction Kit (Applied Biosystems). The product of the sequencing was compared with the nucleotide sequence registered with GenBank. RT-PCR of GAPDH was similarly carried out, except that annealing was carried out at 55° C. and an amplification cycle was repeated 23 times.

(3) RT-PCR Specific for UPIII-F (Complete) and UPIII-A (Incomplete)

In order to specifically detect UPIII-F, the antisense primer UPK3-A4 (SEQ ID NO: 22) was designed in the exon 4 sequence. The sense primer for selectively amplifying UPIII-A was designed as UPK3-AL1 (SEQ ID NO: 23) such that the 5' terminus is in exon 3, and the 3' terminus skips exon 4 and have the first 4 residues in exon 5. UPIII-F-specific PCR was carried out using the sense primer UPK3-SF (SEQ ID NO: 21) and the antisense primer UPK3-A4 (SEQ ID NO: 22) (final concentration: 0.2 pmol/μl), and annealing was carried out at 62° C. UPIII-A-specific PCR was carried out using the sense primer UPK3-AL1 (SEQ ID NO: 23) and the antisense primer UPK3-A2 (SEQ ID NO: 20) (final concentration: 0.2 pmol/μl), and annealing was carried out at 67° C. All the (4) Subcloning of UPIII-F and UPIII-A The PCR products of UPIII-F and UPIII-A amplified by RT-PCR were subcloned into the pCR4-TOPO plasmid vector using the TOPO TA Cloning Kit for Sequencing (Invitrogen), and these plasmids were purified using the Quantum Prep Plasmid Miniprep Kit (BIO-RAD).

(5) Quantitative PCR

Real-time PCR was carried out using the LightCycler-FastStart DNA Master SYBER GREEN I (Roche Diagnostics). In accordance with the recommended protocol, 2 μl each of cDNA sample solution was placed into 20 μl of reaction solution. In the case of real-time PCR of UPIa, UPIb, and UPII, annealing was carried out at 62° C. using UPK1A-S2 (SEQ ID NO: 12) and UPK1A-AI (SEQ ID NO: 11), UPK1b-S2 (SEQ ID NO: 15) and UPK1b-A1 (SEQ ID NO: 16), and UPK2-SI (SEQ ID NO: 17) and UPK2-AI (SEQ ID NO: 18) (final concentration: 0.2 pmol/μl) as the sense and the antisense primers, respectively. Real-time PCR of UPIII-F and that of UPIII-A were carried out under the same conditions as those of specific RT-PCR. After the amplification reaction of 45 cycles, the melting curve was examined at a temperature higher by 7° C. than the annealing temperature. The control DNA for quantification was prepared by purifying uroplakin DNA obtained by RT-PCR for direct sequencing, measuring the concentration using a spectrophotometer, and gradually diluting the purified uroplakin DNA. GAPDH was subjected to quantitative PCR in the same manner. The primers used in real-time PCR are also shown in Table 1.

(6) Data Analysis

Based on the results obtained by quantitative PCR, all the expression levels of uroplakin mRNAs in samples obtained from VUR patients were compared with those obtained from control samples. The results of comparison were statistically analyzed via the Mann-Whitney U test ($p<0.05$: significantly different). In order to examine the diagnostic utility of UPIII mRNA quantification in urine samples, the ROC curve was prepared to set the optimal cut off value, and sensitivity and specificity were determined.

Results (1) Examination of primer specificity via direct sequencing of UPIa, UPIb, UPII, and UPIII and detection of UPIII-A Full-length UPIa, UPIb, UPII, and UPIII were amplified by RT-PCR from the cDNA obtained from tissues obtained from patients with VUR and then electrophoresed. Thereafter, bands were cleaved and subjected to direct sequencing. The product of sequencing was compared with the nucleotide sequence registered with the database, and all the primers were found to be template-specific. The PCR product of UPIII was subjected to agarose gel electrophoresis, and a band was observed in a region somewhat lower than the expected band (a low molecular weight region). As a result of direct sequencing, this PCR product was found to be a splicing variant of UPIII (UPIII-A) completely lacking exon 4 (the region composed of 83 nucleotides between nucleotide 521 and nucleotide 603 of the sequence as shown in SEQ ID NO: 7) of 6 exons in total of UPIII (SEQ ID NO: 9). In the nucleotide sequence as shown in SEQ ID NO: 9, a protein-encoding region was deduced to be a region composed of nucleotides 33 to 671, and the protein encoded thereby was deduced to have the amino acid sequence as shown in SEQ ID NO: 26.

(2) Design of Primers Specific for UPIII-F and UPIII-A and Examination of Their Specificity In order to selectively detect UPIII-F or UPIII-A via RT-PCR, each specific primer were designed and their specificity were examined. DNA encoding full-length UPIII-F and UPIII-A was subcloned into a plasmid vector, and PCR was carried out using this plasmid as a template and each specific primer. As a result, the UPIII-A-specific primer reacted with the UPIII-A plasmid; however, no band was observed via PCR wherein the UPIII-F plasmid was used as a template. UPIII-F-specific primer reacted selectively with the UPIII-F plasmid. Accordingly, specificity of the primers for UPIII-F and UPIII-A respectively was verified.

Figure 2:
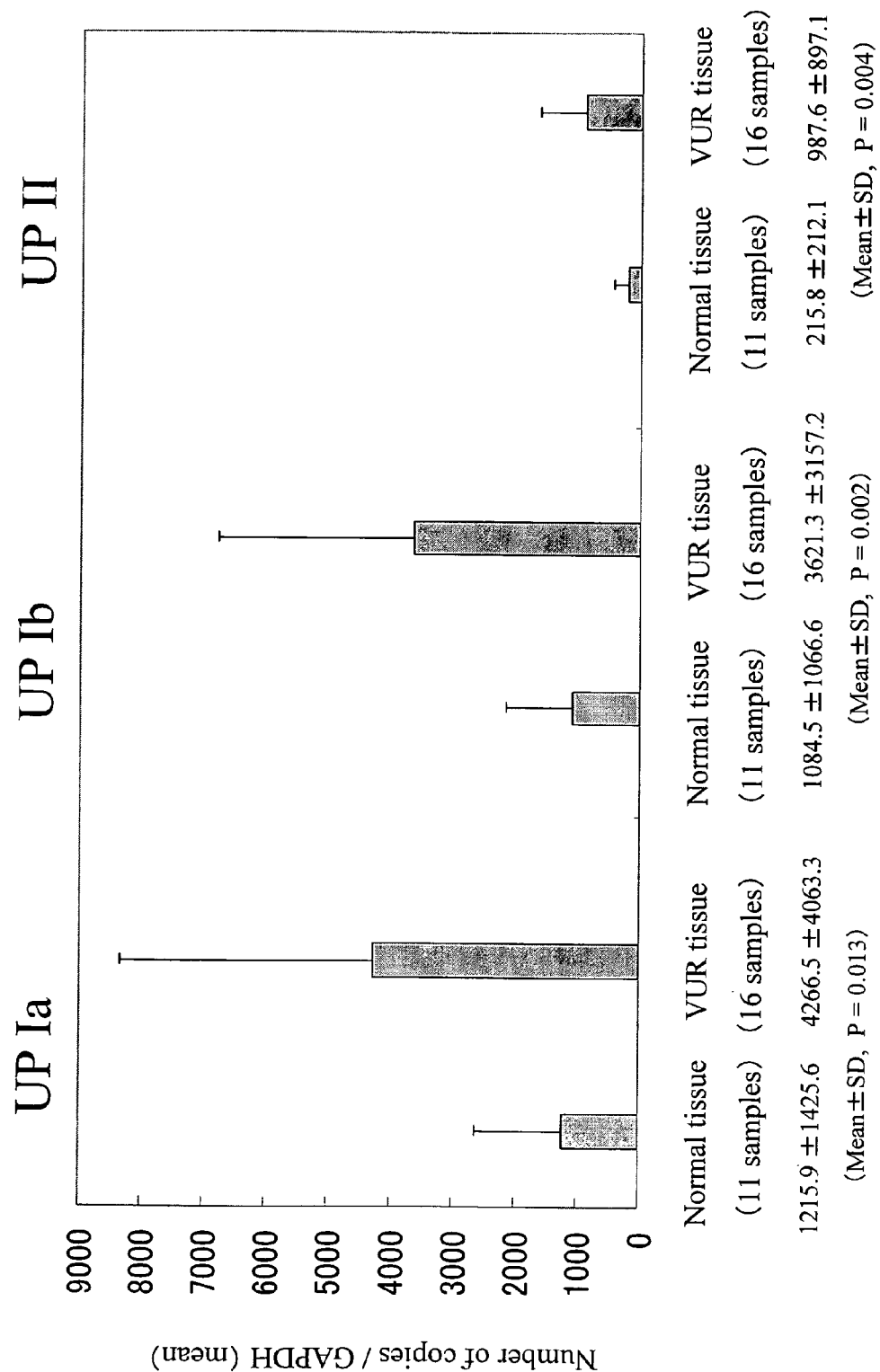
FIG. 2 shows the expression levels of uroplakin Ia, Ib, and II mRNAs in tissues.

(3) Comparison of Expression Level of Uroplakin mRNA in Tissues Obtained from Patients with VUR and in Normal Urothelial Tissues In order to quantify and compare the expression levels of UPIII mRNA in the bladder epithelial tissues obtained from patients with VUR and in normal urothelial tissues, 20 tissue samples obtained from patients with VUR and 11 normal samples were subjected to quantitative PCR. The expression level of UPIII-F and that of UPIII-A were calculated in terms of numbers of copies and then standardized with the expression levels of GAPDH in the samples that had been similarly quantified. As a result, the mean±SD of the expression level of UPIII-F mRNA and that of UPIII-A mRNA per ng of GAPDH in the tissues obtained from patients with VUR were 5969.60±17642.50 and 12.51±26.35, respectively. In contrast, these figures were 131.19±165.42 and 1.37±2.04, respectively, in normal tissues. This indicates that both UPIII-F and UPIII-A were overexpressed in tissues obtained from patients with VUR. Among the 20 tissue samples obtained from patients with VUR, 4 samples exhibited abnormally high levels of expression, i.e., 7,000 or more copies of UPIII-F and 13 or more copies of UPIII-A. Besides these 4 special samples, the expression levels of UPIII-F and UPIII-A were significantly enhanced in tissues obtained from patients with VUR ($p<0.0001$ and $p=0.023$, respectively) (see Table 2 and FIG. 1). Other types of uroplakin were subjected to similar comparison, and all uroplakin mRNAs were found to be overexpressed in tissues obtained from patients with VUR (see Table 3 and FIG. 2).

TABLE 2

| | Mean ± SD (number of copies per unit GAPDH) | |
|---|---|---|
| | UPIII-F | UPIII-A |
| Normal tissue (11 samples) | 131.19 ± 165.42 | 1.37 ± 2.04 |
| Tissues obtained from patients with VUR (16 samples) | 987.62 ± 897.12 | 4.60 ± 2.98 |
| | * p < 0.0001 | * p = 0.023 |

* $p < 0.05$: significant
Except for 4 samples exhibiting abnormally high expression levels in tissues obtained from patients with VUR

TABLE 3

| | Mean ± SD (number of copies per unit GAPDH) | | |
|---|---|---|---|
| | UPIa | UPIb | UPII |
| Normal tissue (11 samples) | 1215.9 ± 1425.66 | 1084.48 ± 1066.56 | 215.75 ± 212.14 |
| Tissues obtained from patients with VUR (16 samples) | 4266.51 ± 4063.31 | 3621.34 ± 3157.20 | 882.77 ± 761.44 |
| | * p = 0.013 | * p = 0.002 | * p = 0.004 |

* $p < 0.05$: significant
Except for 4 samples exhibiting abnormally high expression levels in tissues obtained from patients with VUR Differences in the expression levels of uroplakin mRNAs caused by the age and the site of sampling from the urothelial tissues were also examined. The expression levels in tissues obtained from adult patients with VUR were not different from those obtained from child patients with VUR, and substantially the same level of overexpression was observed. Also, the expression levels in normal bladder tissues were not different from those in normal tissues in the upper urinary tract.

Figure 3:
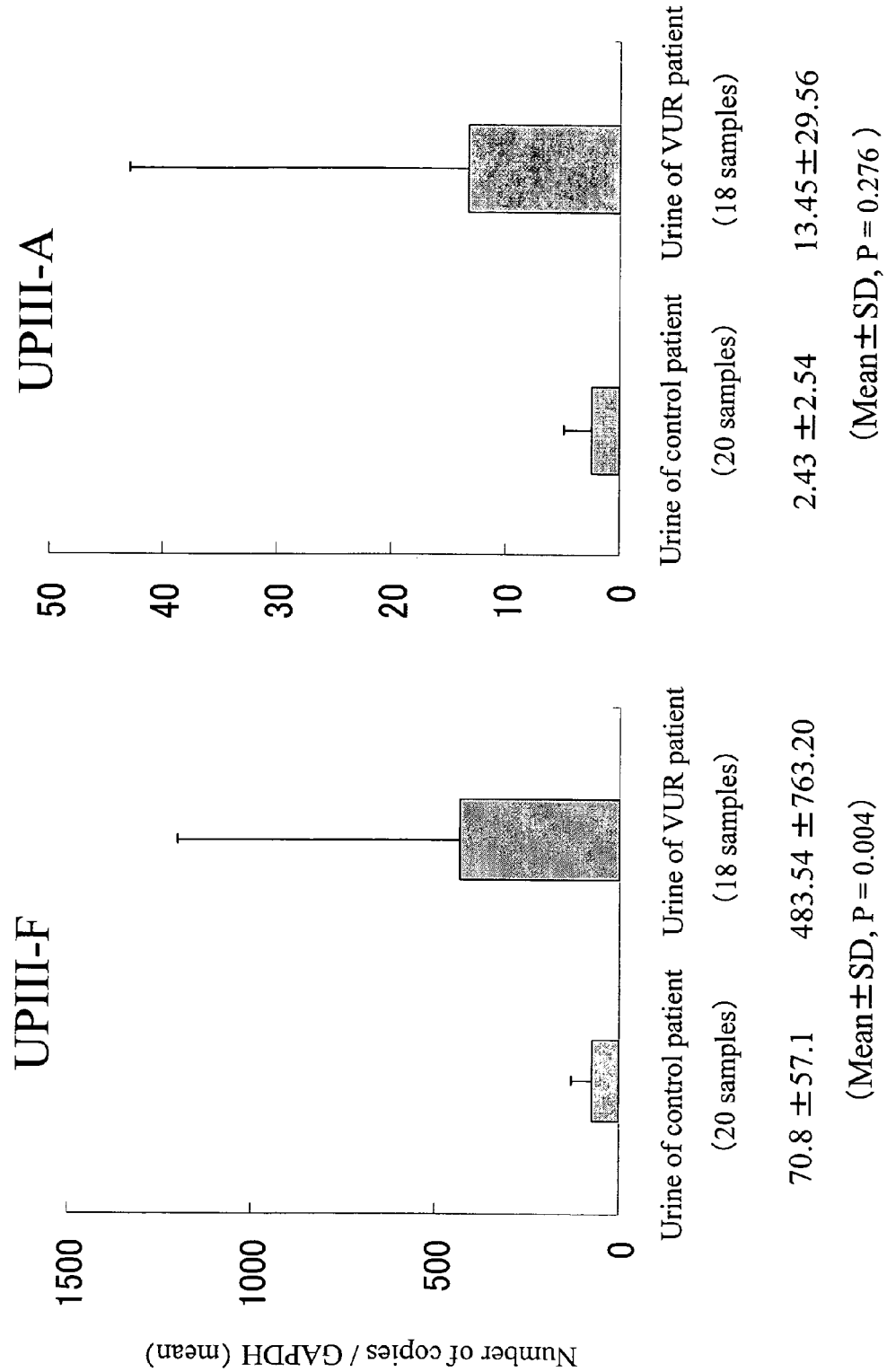
FIG. 3 shows the expression level of uroplakin III mRNA in exfoliated cells in urine.
Figure 4:
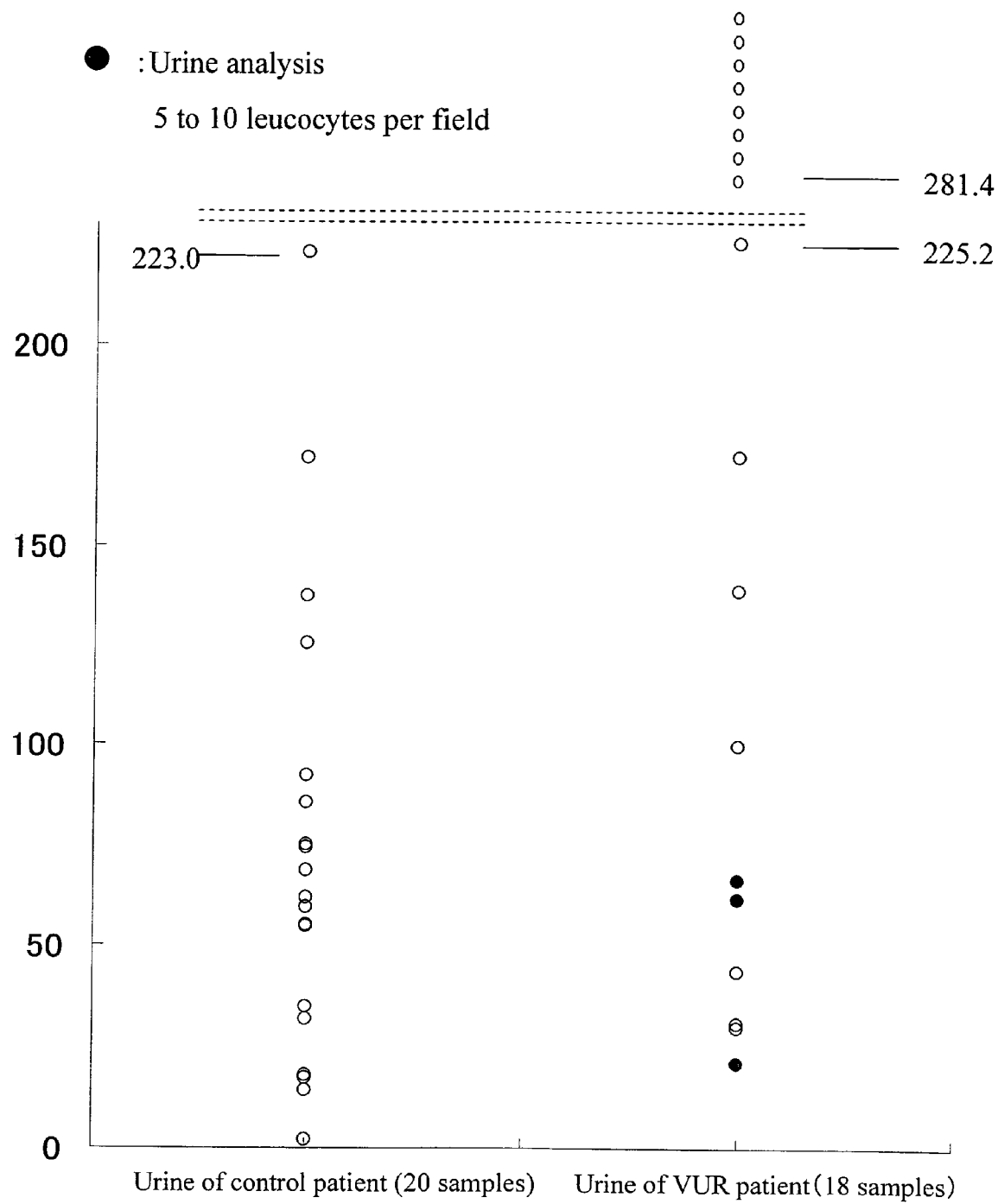
FIG. 4 shows the expression level of complete uroplakin III mRNA in exfoliated cells in urine.
Figure 5:
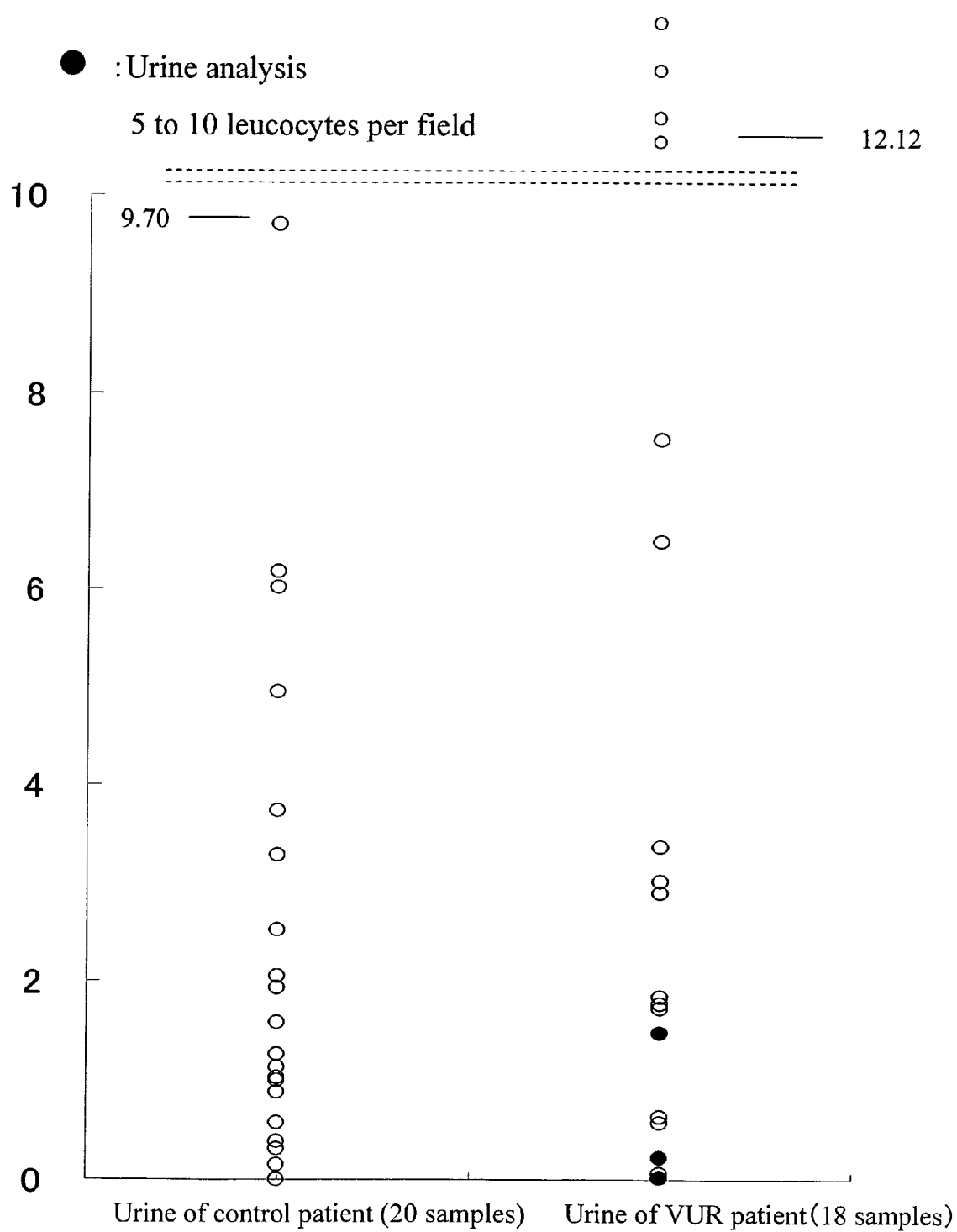
FIG. 5 shows the expression level of variant uroplakin III mRNA in exfoliated cells in urine.

(4) Comparison of Expression Levels of UPIII mRNA in Exfoliated Cells in Urine of Patients with VUR and in Urine of Healthy Volunteers Whether or not UPIII-F and UPIII-A, mRNA of which was found to be overexpressed in tissues obtained from patients with VUR, could be detected with the use of urine specimens was examined. Urine specimens obtained from 18 patients with VUR and urine specimens obtained from 20 control patients were subjected to real-time PCR to quantify UPIII-F and UPIII-A. Three specimens exhibiting mild pyuria (defined by a leukocyte count of 5 to 10 cells per field) were included in 18 specimens obtained from patients with VUR. As with the case using tissue samples, the detection results of the samples were standardized with the expression levels of GAPDH mRNA, and the numbers of copies thereof were calculated. As a result, the medians of the expression levels of UPIII-F mRNA per ng of GAPDH were 198.6 and 63.9 in urine samples obtained from patients with VUR and control urine samples, respectively. The mean±SD values were 438.54±763.20 and 70.8±57.1 ($p=0.004$) in urine samples obtained from patients with VUR and control urine samples, respectively. The expression levels were statistically significantly enhanced in the urine samples obtained from patients with VUR. Concerning UPIII-A mRNA, the medians were 2.37 and 2.48, and the mean±SD values were 13.45±29.56 and 2.43±2.54 (p=0.276), respectively (see Table 4 and FIGS. 3, 4, and 5). The cut off value for VUR detection was set based on the quantitative value of the expression level of UPIII-F mRNA. The optimal cut off value obtained from the ROC curve was 95. Based on such setting, the sensitivity was 66.7% and the specificity was 80% (the number of positive specimens: 12 out of 18 VUR specimens; 4 out of 20 control specimens). The quantitative values of 3 pyuria specimens among the VUR specimens were equal to or lower than the cut off value. These results could be false negatives due to contamination with GAPDH mRNA derived from leucocytes other than the urothelium. Accordingly, these 3 specimens were excluded, and the sensitivity was determined to be 80% (the number of positive specimens: 12 out of 15 VUR specimens).

TABLE 4

| | Mean ± SD (number of copies per unit GAPDH) | |
|---|---|---|
| | UPIII-F | UPIII-A |
| Urine of control patients (20 specimens) | 70.8 ± 57.1 | 2.43 ± 2.54 |
| Urine of patients with VUR (18 specimens) | 438.54 ± 763.20 | 13.45 ± 29.56 |
| | *p = 0.004 | *p = 0.276 |

* p < 0.05: significant
Except for 4 samples exhibiting abnormally high expression levels in tissues obtained from patients with VUR Example 2

Expression Level of Uroplakin mRNA in Interstitial Cystitis (IC)

Targets

Bladder epithelial tissue samples (4 specimens) of patients with IC obtained via biopsy of bladder mucosa and urothelial tissue samples (5 specimens) of control patients (i.e., urologic patients with no obvious abnormalities in urinary tract transitional epithelia such as prostatic hyperplasia or prostate carcinoma) were used. Samples were preserved at −80° C. immediately after sampling.

Method

In the same manner as in the experiment using tissues obtained from patients with VUR, mRNA sampling, cDNA synthesis, and UPIII-A-specific RT-PCR were carried out. The PCR product was electrophoresed on 2% agarose gel to which ethidium bromide had been added, the visualized bands were scanned using Luminous Imager version 1.2 for Macintosh (AISIN Cosmos R&D Co.), the bands were semi-quantified using Scion Image software (Scion Co.), and the semiquantified values were standardized with the expression levels of GAPDH in the samples. Based on these results, the expression levels of UPIII-Am mRNA were compared between tissue samples obtained from patients with IC and normal tissue samples. Statistical analysis was carried out via the Mann-Whitney U test (p<0.05: significantly different).

Results

Figure 6:
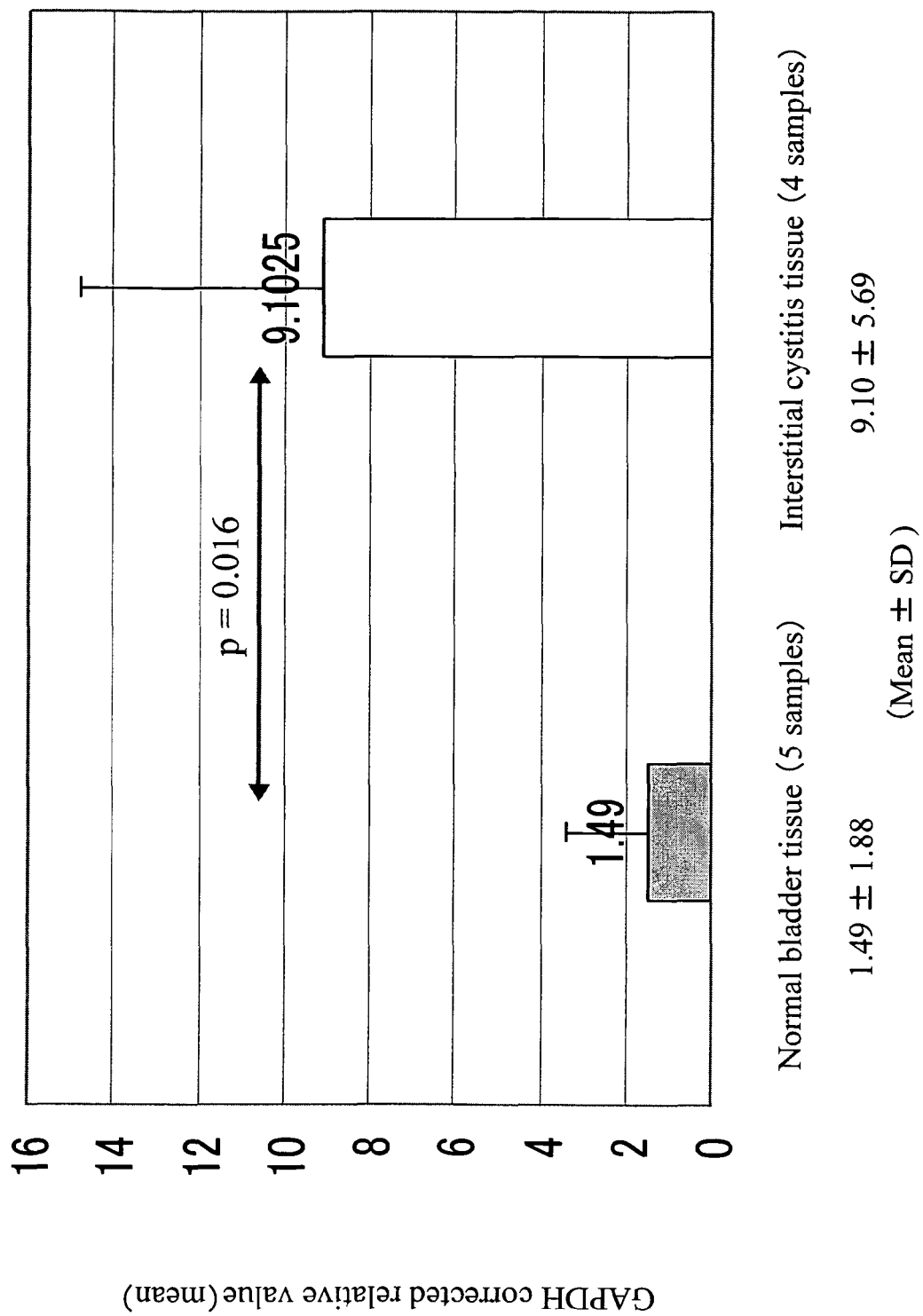
FIG. 6 shows the expression level of uroplakin III mRNA in interstitial cystitis tissues.

As in the case of tissues obtained from patients with VUR, 4 bladder epithelial tissue samples obtained from patients with IC and 5 normal urothelial tissue samples were subjected to UPIII-A-specific RT-PCR, and the expression levels of mRNA were semiquantified and compared, in order to assay the expression levels of UPIII-A mRNA in the tissue samples obtained from patients with IC. The mean±SD values of the relative expression levels of UPIII-A mRNA standardized with GAPDH were 9.10±5.69 and 1.49±1.88 in the tissues obtained from patients with IC and in the normal tissues, respectively. This indicates that the expression levels were significantly enhanced in the tissues obtained from patients with IC (p=0.016, see FIG. 6).

Thus, overexpression of all 4 types of uroplakin families that had previously been known and a novel splicing variant of UPIII that had been discovered in the present invention was observed to a greater extent in tissues obtained from patients with VUR than in normal tissues. Quantification of mRNA could be carried out with the use of urine samples via quantitative PCR. As with the case using the tissue samples, mRNA was overexpressed in exfoliated cells in the urine of patients with VUR at a statistically significant level. Accordingly, detection of the expression level of uroplakin mRNA in exfoliated cells in urine, particularly detection of the expression levels of UPIII-F mRNA, was found to be effective as a simple screening method utilizing urines obtained from patients with VUR.

Since overexpression of UPIII mRNA was observed in the bladder epithelial tissues obtained from patients with IC, detection of the expression levels of uroplakin mRNA in exfoliated cells in urine was found to be effective for patients with IC as a simple screening method utilizing urine.

All publications, patents, and patent applications cited herein are incorporated herein by reference in their entirety.

What is claimed is:

1. A method of determining an increased risk of vesicoureteral reflux (VUR) in a human comprising:
   (A) obtaining a sample of epithelial cells obtained from the urinary tract of a human; detecting mRNA that encode uroplakin in said sample, wherein said mRNA that is detected is at least one of the uroplakin from the group consisting of UPIa, UPIb, UPII, UPIIIA, and UPIIIF; and detecting an increased level of the mRNA as compared to mRNA levels found in normal epithelial cells from an urinary tract of control humans, wherein an increased level of the mRNA indicates an increased risk of VUR, or
   (B) obtaining a sample of epithelial cells obtained from urine of a human;
   detecting UPIIIF mRNA in said sample; and detecting an increased level of UPIIIF mRNA as compared to the level found in normal epithelial cells taken from urine of control humans, wherein an increased level of UPIIIF mRNA indicates an increased risk of VUR.

2. A method of determining an increased risk of interstitial cystitis (IC) in a human comprising:
   obtaining a sample of epithelial cells obtained from the urinary tract of a human;
   detecting mRNA that encode uroplakin in said sample, wherein said mRNA that is detected is at least one of the uroplakin from the group consisting of UPIa, UPIb, UPII, UPIIIA, and UPIIIF;
   and detecting an increased level of the mRNA as compared to levels found in normal epithelial cells from a urinary tract of control humans, wherein an increased level of the mRNA indicates an increased risk of IC.

3. The method of claim 1 or 2, wherein the uroplakin mRNA in the sample obtained from said subject is detected using two oligonucleotide primers, each comprising 15-50 continuous nucleotides for specifically amplifying the polynucleotides that encode uroplakin.

4. The method of claim 1 or 2, wherein the uroplakin mRNA in the sample obtained from said subject is detected using a polynucleotide probe comprising 15-50 continuous nucleotides that specifically hybridizes with the polynucleotides that encode uroplakin.

5. The method of claim 1 or 2, wherein said epithelial cells obtained from the urinary tract are obtained from bladder epithelial tissue.

* * * * *